United States Patent
Grinstaff et al.

(10) Patent No.: US 6,696,081 B2
(45) Date of Patent: Feb. 24, 2004

(54) CARBOHYDRATE BASED LIPID COMPOSITIONS AND SUPRAMOLECULAR STRUCTURES COMPRISING SAME

(75) Inventors: Mark W. Grinstaff, Durham, NC (US); Geoffrey S. Hird, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/877,391

(22) Filed: Jun. 8, 2001

(65) Prior Publication Data

US 2002/0035082 A1 Mar. 21, 2002

Related U.S. Application Data
(60) Provisional application No. 60/210,694, filed on Jun. 9, 2000.

(51) Int. Cl.$^7$ .............................. A61K 9/27; C07F 9/02
(52) U.S. Cl. ...................... 424/450; 548/413; 514/23; 514/25; 514/44; 536/117; 536/18.7; 549/6
(58) Field of Search .............................. 424/450, 176.1; 514/25, 44, 23; 530/341.1; 536/117, 18.7; 548/413; 549/6

(56) References Cited

U.S. PATENT DOCUMENTS

| | | | |
|---|---|---|---|
| 3,956,278 A | 5/1976 | Prey | |
| 4,426,330 A | 1/1984 | Sears | |
| 4,481,196 A | * 11/1984 | Teraji | ........................... 514/25 |
| 4,897,474 A | 1/1990 | Bickert | |
| 5,830,430 A | 11/1998 | Unger et al. | |
| 6,235,772 B1 | 5/2001 | Packer et al. | |

OTHER PUBLICATIONS

Nishida et al (Tetrahedron Letters (1994) 35(30): 5465–5468.*
Noda et al (Chemical and Pharmaceutical Bulletin (1993) 41(10): 1733–1737).*
Neumann et al (J. Amer. Chem. Soc. (1989) 111(12): 4270–4277).*
Ahmad et al., "Cyclopentanoid Analogs of Dipalmitoys Phosphatidic Acid: Effect of Backbone Geometry on Thermotropic Properties," Chem. Phys. Lipids, p. 231–243, (1990).
Blume et al., "A Calorimetric Study of the Thermotropic Behaviour of 1,2–Dipentadecylmethylidene Phospholipids," Biochim. Biophys. Acta., vol. 640 p. 609–618, (1981).
Engel, "Phosphonates as Analogues of Natural Phosphates," Chem. Rev., p. 349–367, (1977).
Srisiri et al., "Selective Polymerization of Double–Diene Lipid Assemblies: a Novel Approach to Ladder–Like Polymers." J. Am. Chem. Soc., p. 11327–11328, (1996).
Thomas et al., "Phoaphonate Lipid Tubules," J. Am. Chem. Soc., p. 12178–12186, (1998).
Trauble et al., "Electrostatic Effects on Lipid Phase Transitions: Membrane Structure and Ionic Environment," Proc. Natl. Acad. Sci. USA, vol. 71 (No. 1), p. 214–219, (1974).
Van Dijck et al., "Comparative Studies on the Effects of pH and Ca2+ on Bilayers of Various Negatively Charged Phospholipids and Their Mixtures with Phosphatidylcholine," Biochim. Biophys. Acta., vol. 512 p. 84–96, (1978).

* cited by examiner

Primary Examiner—Dave T. Nguyen
Assistant Examiner—Richard Schnizer
(74) Attorney, Agent, or Firm—Jenkins, Wilson & Taylor, P.A.

(57) ABSTRACT

Novel lipid compounds and compositions comprising carbohydrate backbones are used to make supramolecular structures such as vesicles, liposomes (single lamellar, multilamellar, and giant), micelles, hexagonal phases, microemulsions and others. The novel compositions and supramolecular structures may be combined with active agents such as contrast agents and bioactive agents (e.g., therapeutic and diagnostic agents) in delivery methods.

72 Claims, 1 Drawing Sheet

CARBOHYDRATE BASED LIPID COMPOSITIONS AND SUPRAMOLECULAR STRUCTURES COMPRISING SAME

CROSS REFERENCE TO RELATED APPLICATIONS

This application is based on and claims priority to U.S. Provisional Application Serial No. 60/210,694, filed Jun. 9, 2000, herein incorporated by reference in its entirety.

TECHNICAL FIELD

The present invention relates generally to lipid compositions. More particularly, the present invention relates to lipid compositions comprising a carbohydrate backbone, and to supramolecular structures comprising the same. In a preferred embodiment, the lipid composition further comprises a phospholipid.

Table of Abbreviations

| | |
|---|---|
| Å | angstrom(s) |
| aq | aqueous |
| CF | carboxyfluorescein |
| CBZ | carbobenzoxy group |
| $CH_2Cl_2$ | methylene chloride |
| cm | centimeter(s) |
| $^{13}$C-NMR | carbon 13-nuclear magnetic resonance |
| COPD | chronic obstruction pulmonary disease |
| COSY | correlation spectroscopy |
| DAPC | methyl-2,3-di-O-arachadonyl-b-D-5-phosphocholine |
| DARPC | methyl-2,3-di-O-arachadonyl-b-D-ribo-5-phosphocholine |
| DCC | dicyclohexylcarbodiimide |
| dd | double deionzied |
| dev | deviation |
| DI | deionized |
| DLPA | dilauroyl phosphatidic acid |
| DLPC | 1,2-dilauroyl-sn-glycero-3-phosphocholine |
| DLR-Lys | 1-methoxy-2,3-dilauroyl-ribo-5 lysine |
| DLRPA | bis-(2,3-lauroyl)-1-methoxy-5-ribo-phosphatidic acid |
| DLRPC | methyl-2,3-di-O-lauroyl-b-D-ribo-5-phosphocholine |
| DMAP | dimethylaminopyridine |
| DMF | dimethyl furan |
| DMPC | dimyristyl phosphocholine |
| DMRPC | methyl-2,3-di-O-myristoyl-b-D-ribo-5-phosphocholine |
| DPPC | dipalmitoylphosphatidyl-choline |
| DPTS | 4-dimethylaminopyridium-p-toluenesulfate |
| EtAc | ethyl acetate |
| g | gram |
| h or hr or hrs | hour(s) |
| hex | hexane |
| HMQC | Heteronuclear Multiple-Quantum Correlation |
| $^1$H-NMR | hydrogen 1-nuclear magnetic resonance |
| Hz | Hertz |
| ILD | interstitial lung disease |
| J | Joule |
| kcal | kilocalorie(s) |
| $L_\alpha$ | liquid crystalline |
| $L_\beta$ | lamellar gel |
| M | Molar |
| m | meter |
| MeOH | methyl alcohol |
| MDSC | modulated differential scanning calorimetry |
| MHz | Megahertz |
| Min | minute |
| Mg | milligram(s) |
| mL | milliliter(s) |
| mm | millimeter(s) |
| mmol | millimolar |
| mol % | mole percent |
| MRI | magnetic resonance imaging |
| MS | mass spectroscopy |
| N | Normal |
| nm | nanometer(s) |
| $P_\beta$ | rippled gel |
| PBS | phosphate buffered saline |
| PEG | polyethylene glycol |
| PET | positron emission tomography |
| $PLA_2$ | phospholipase $A_2$ |
| $^{31}$P-NMR | phosphorus 31-nuclear magnetic resonance |
| ppm | parts per million |
| PSI | pounds per square inch |
| Pyr | pyrimidine |
| Rpm | revolutions per minute |
| std | standard |
| t | time |
| THF | tetrahydro furan |
| TLC | thin layer chromatography |
| $T_m$ | phase-transition temperature |
| TrCl | trityl chloride |

BACKGROUND ART

A lipid compound, including particularly a phospholipid compound, typically comprises a hydrophilic head group, a lipophilic tail group, a backbone, and linker moieties between the head group and backbone and tail group and backbone, respectively. The most common backbone for a phospholipid, including particularly naturally occurring phospholipids, is a glycerol backbone.

In the art, many different variations of phospholipids have been synthesized by changing linkers, head groups and tail groups. See e.g. U.S. Pat. No. 4,426,330 to Sears; Thomas, B. N.; et al., *J. Am. Chem. Soc.* 1998, 120, 12178–12186; Srisiri, W.; et al., *J. Am. Chem. Soc.* 1996, 118, 11327–11328. The glycerol backbone of a phospholipid compound has also been modified. Two major classes of non-glycerol-based synthetic phospholipids exist in the art, the phosphonolipids and the cyclopentane-based phospholipids. See e.g. Engel, R. *Chem. Rev.* 1977, 77, 349–367; Bittman, R. Chemical Synthesis of glycerophospholipds and their analogs; Bittman, R., Ed.; CRC Press: Boca Raton, Fla., United States of America, 1999, pp 185–207. These modified phospholipids exhibit different physical properties from their glycerol-based analogs, indicating the importance of backbone on bilayer structure. Thus, the preparation and characterization of lipids having modified backbones represents an ongoing need and effort in the art.

Phospholipid structure plays an important role in determining the supramolecular structures formed in solution. Israelachvili, J. N. *Intermolecular and Surface Forces*; Academic Press Inc.: San Diego, 1992. Specifically, the hydrophilic charged head and hydrophobic tail(s) groups influence the supramolecular and bilayer structure formed, as well as the physical and mechanical properties of these bilayers. For example, the properties of negatively charged phospholipids and their corresponding supramolecular structures can also be dependent upon environmental conditions such as pH and cation concentration. Van Dijck, P. W. M.; et al., *Biochim. Biophys. Acta.* 1978, 512, 84–96. Bilayer structures formed from anionic phospholipids are also dependent on the chemical constituents of the amphiphilic compound as demonstrated by anionic phospholipids containing a cyclopentane or a dipenta-decylmethylidene backbone instead of glycerol. Ahmad, T. Y.; et al., *Chem. Phys. Lipids* 1990, 55, 231–243; Blume, A.; Eibl, H. *Biochim. Biophys. Acta.* 1981, 640, 609–618.

Three conformational changes occur in a bilayer membrane at the critical gel-liquid crystalline phase-transition temperature ($T_m$): rotational isomers from all-trans to multiple gauche in the tails of the molecule, rapid lateral diffusion within the bilayer membrane, and bilayer area expansion. All three of these factors are important in establishing the phase-transition temperature. For example, electrostatic interactions affect bilayer area. With an increase in phospholipid charge, inter-phospholipid repulsions increase, yielding an increase in bilayer area, and a decrease in $T_m$. Trauble, H.; Eibl, H. *Proc. Nat Acad. Sci. USA* 1974, 71, 214–219. Variations in pH are also known to alter the $T_m$, and this effect is particularly significant in those pH regions similar to the pKa's of the head group. Sensitivity to the aqueous solution in which the bilayer resides is important physiologically, since changes in pH and ion concentration alter bilayer physical properties. Van Dijck, P. W. M.; et al., *J. Biochim. Biophys. Acta.* 1978, 512, 84–96. The manipulation of these and other characteristics and variables in a supramolecular structure composition comprising a phospholipid thus represents an ongoing research effort and unsolved problem in the art.

This present invention pertains to a unique class of lipids where the glycerol backbone is replaced with a carbohydrate. In a series of preferred embodiments, zwitterionic, anionic, and cationic carbohydrate-based phospholipids were synthesized and characterized, and novel functionalities were observed. Thus, the present invention meets a long-felt and continuing need in the art for a novel lipid compound, a novel supramolecular structure comprising the same, and for methods of making and using the same.

SUMMARY OF THE INVENTION

A lipid compound comprising:

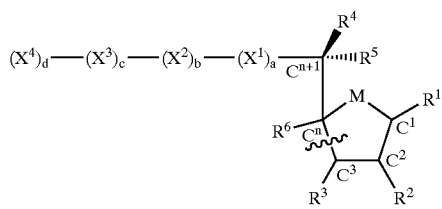

Formula (I), where each carbon of $C^{n+1}$ and $C^1$ to $C^n$ is a stereochemical center; each carbon of $C^1$ to $C^n$ is a member of a heterocyclic ring containing M; n=4, 5, 6 or 7; $R^1$, $R^2$, $R^3$, $R^4$, $R^5$ and $R^6$ are the same or different, and are selected from the group consisting of H, OH, amine, thiol, methoxy, straight or branched chain ester of 6–50 carbon atoms, straight or branched chain silane of 6–50 carbon atoms, straight or branched chain amide of 6–50 carbon atoms, straight or branched chain urea of 6–50 carbon atoms, straight or branched chain urethane of 6–50 carbon atoms, straight or branched chain carbonate of 6–50 carbon atoms, straight or branched chain sulfate of 6–50 carbon atoms, straight or branched chain thiol-urethane of 6–50 carbon atoms, straight or branched chain phosphate of 6–50 carbon atoms, straight or branched chain amine of 6–50 carbon atoms, straight or branched chain thio-urea of 6–50 carbon atoms, straight or branched chain thio-ether of 6–50 carbon atoms, straight or branched chain thio-ester of 6–50 carbon atoms, straight or branched chain ether of 6–50 carbon atoms, and any combination thereof, wherein the chain is fully saturated, fully unsaturated or any combination thereof; M and $X^1$ the same or different and are O, S, or N—$R^7$, wherein $R^7$ is H, a lower alkane, a chain as recited for $R^1$, $R^2$, $R^3$, Se or any isoelectronic species of oxygen and a=0, 1, 2, 3, 4, 5, 6, 7, 8, 9, or 10; $X^2$ is phosphonate, phosphate, boronophosphate, thiophosphate, or selenophosphate and b is 0, 1, 2, 3, 4, 5, 6, 7, 8, 9 or 10; $X^3$=methylene or a monomer selected from the group consisting of an ether, an ester, an amine, acrylic acid, amino acid, a nucleic acid, or a monosaccharide, and c=0, 1, 2, 3, 4, 5, 6, 7, 8, 9, 10, 11, 12, 13, 14, 15, 16, 17, 18, 19, or 20; $X^4$=hydroxide, N-succinyl derivative, a monomer selected from the group consisting of an amine, an ether, an ester, an amino acid, monosaccharide, and a nucleic acid, N—$(R^8)_e$ where $R^8$ is hydrogen or methylene chain of 1–20 carbons, or cyclic forms thereof and d=0, 1, 2, 3, 4, 5, 6, 7, 8, 9, 10 and e=1, 2 or 3.

The present invention also provides a novel supramolecular structure comprising a compound of Formula (I). The present invention also provides processes of making and methods of using the novel compounds and compositions.

Accordingly, it is an object of the present invention to provide a novel lipid compound, and a novel supramolecular structure composition comprising the compound. This and other objects are achieved in whole or in part by the present invention.

Some of the objects of the invention having been stated herein above, other objects will become evident as the description proceeds when taken in connection with the accompanying drawings and Laboratory Examples as best described herein below.

DETAILED DESCRIPTION OF THE INVENTION

Figure 1:
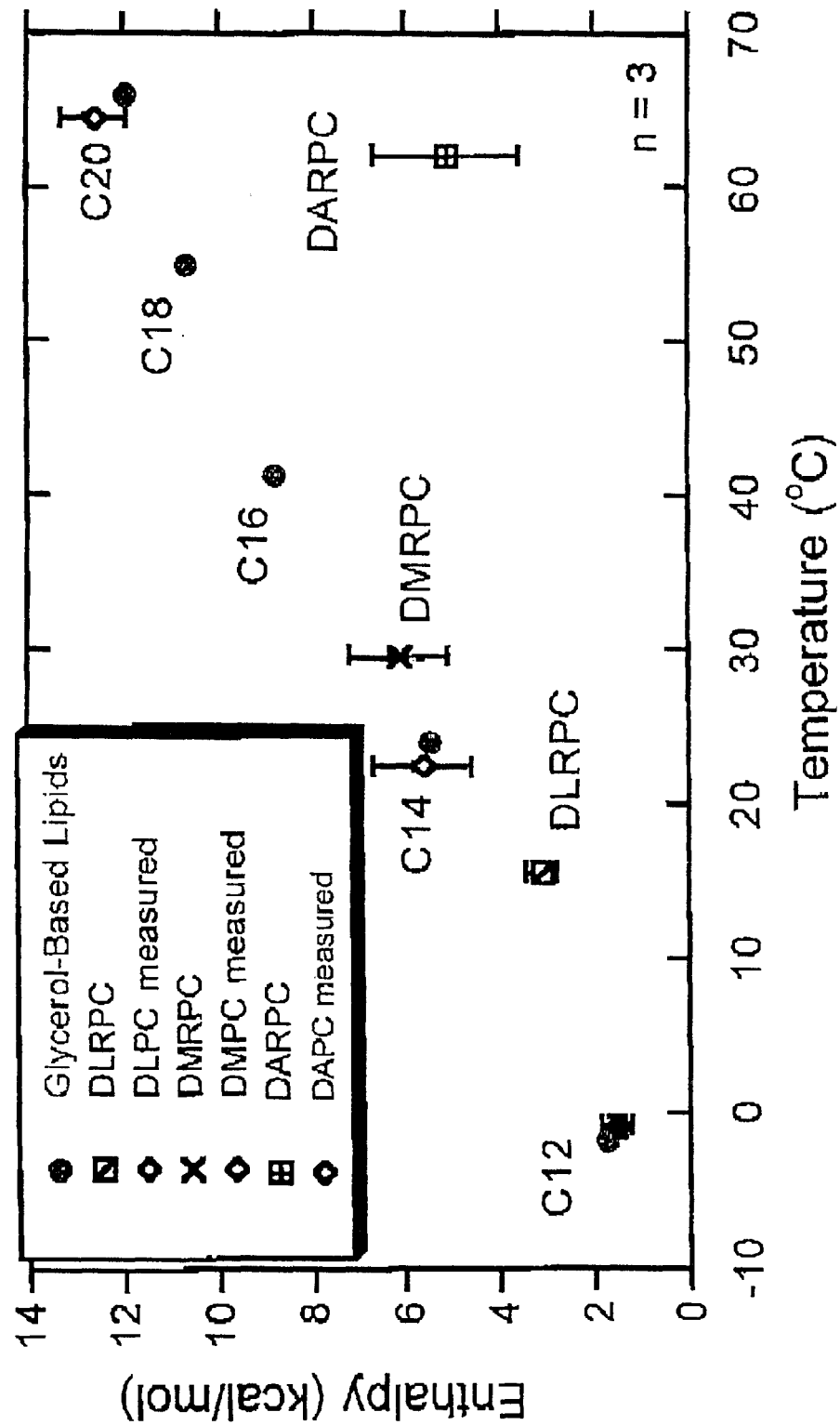
FIG. 1 is a graph showing the relationship between $T_m$ and enthalpy for the ribose phospholipid.

A novel carbohydrate-based lipid compound is disclosed, which in an appropriate solvent, self-assembles into supramolecular structures. This compound and its supramolecular structures can be used as a novel material for many applications. Supramolecular structures are of interest in the medical, biotechnological, food, cleaning, petroleum, electronics, semiconductors, composites, optics, paints, and cosmetics industries.

The present invention relates to novel carbohydrate based lipids which, among other structures, can form a liposome that can be used to encapsulate or label compounds for applications in drug delivery, delivery of genetic material, medical imaging (sono, Magnetic Resonace Imaging (MRI), X-ray, Positron Emission Tomography (PET)), artificial bloods, cell encapsulation, flavor and fragrance delivery, dyes, and cosmetics. In a preferred embodiment, the lipid is a phospholipid.

In addition to supramolecular structures (e.g. vesicles and liposomes) comprising pure carbohydrate based phospholipids, different compositions with conventional phospholipids such as dimyristyl phosphocholine (DMPC) as well as nucleic acids (e.g. DNA), proteins, surfactants, and combinations thereof, are provided, and their unique properties discerned. The self-assembly of other supramolecular structures formed by the present inventive compounds (such as micelles, vesicles, tubules, hexagonal phases, liposomes, tori, helixes and other such structures) is also provided.

I. Definitions

As employed above and throughout the disclosure, the following terms, unless otherwise indicated, shall be understood to have the following meanings. The following terms thus refer to and can be used to refer to substituents and/or functional groups for a compound of the present invention.

"Alkyl" refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. There can be optionally inserted along the alkyl chain one or more oxygen, silicon, sulphur or substituted or unsubstituted nitrogen atoms, wherein the nitrogen substituent is lower alkyl. "Branched" refers to an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Preferred alkyl groups included branched or straight chain alkyl groups of 6 to 50 carbon, and also include the lower alkyl groups of 1 to about 4 carbons and the higher alkyl groups of about 12 to about 16 carbons.

"Alkenyl" refers to an alkyl group containing at least one carbon—carbon double bond. The alkenyl group can be optionally substituted with one or more "alkyl group substituents". Exemplary alkenyl groups include vinyl, allyl, n-pentenyl, decenyl, dodecenyl, tetradecadienyl, heptadec-8-en-1-yl and heptadec-8,11-dien-1-yl.

"Alkynyl" refers to an alkyl group containing a carbon—carbon triple bond. The alkynyl group can be optionally substituted with one or more "alkyl group substituents". Exemplary alkynyl groups include ethynyl, propargyl, n-pentynyl, decynyl and dodecynyl. Preferred alkynyl groups include the lower alkynyl groups.

"Cycloalkyl" refers to a non-aromatic mono- or multicyclic ring system of about 4 to about 10 carbon atoms. The cycloalkyl group can be optionally partially unsaturated. The cycloalkyl group can be also optionally substituted with an aryl group substituent, oxo and/or alkylene. Representative monocyclic cycloalkyl rings include cyclopentyl, cyclohexyl and cycloheptyl. Preferred multicyclic cycloalkyl rings include adamantyl, octahydronaphthyl, decalin, camphor, camphane, and noradamantyl.

"Aryl" refers to a cyclic aromatic containing about 6 to about 10 carbon atoms. The aryl group can be optionally substituted with one or more aryl group substituents which can be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Acyl" refers to an alkyl-CO— group wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

"Aroyl" means an aryl-CO— group wherein aryl is as previously described. Exemplary aroyl groups include benzoyl and 1- and 2-naphthoyl.

"Alkoxy" refers to an alkyl-O— group wherein alkyl is as previously described. Exemplary alkoxy groups include methoxy, ethoxy, n-propoxy, i-propoxy, n-butoxy and heptoxy.

"Aryloxy" refers to an aryl-O— group wherein the aryl group is as previously described. Exemplary aryloxy groups include phenoxy and naphthoxy.

"Alkylthio" refers to an alkyl-S— group wherein alkyl is as previously described. Exemplary alkylthio groups include methylthio, ethylthio, i-propylthio and heptylthio.

"Arylthio" refers to an aryl-S— group wherein the aryl group is as previously described. Exemplary arylthio groups include phenylthio and naphthylthio.

"Aralkyl" refers to an aryl-alkyl-group wherein aryl and alkyl are as previously described. Exemplary aralkyl groups include benzyl, phenylethyl and naphthylmethyl.

"Aralkyloxy" refers to an aralkyl-O— group wherein the aralkyl group is as previously described. An exemplary aralkyloxy group is benzyloxy.

"Aralkylthio" refers to an aralkyl-S— group wherein the aralkyl group is as previously described. An exemplary aralkylthio group is benzylthio.

"Dialkylamino" refers to an —NRR' group wherein each of R and R' is independently an alkyl group as previously described. Exemplary alkylamino groups include ethylmethylamino, dimethylamino and diethylamino.

"Alkoxycarbonyl" refers to an alkyl-O—CO— group. Exemplary alkoxycarbonyl groups include methoxycarbonyl, ethoxycarbonyl, butyloxycarbonyl and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an H2N—CO— group.

"Alkylcarbamoyl" refers to a R'RN—CO— group wherein one of R and R' is hydrogen and the other of R and R' is alkyl as previously described.

"Dialkylcarbamoyl" refers to R'RN—CO— group wherein each of R and R' is independently alkyl as previously described.

"Acyloxy" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

"Alkylene" refers to a straight or branched bivalent aliphatic hydrocarbon group having from 1 to about 30 carbon atoms. The alkylene group can be straight, branched or cyclic. The alkylene group can be also optionally unsaturated and/or substituted with one or more "alkyl group substituents." There can be optionally inserted along the alkylene group one or more oxygen, sulphur or substituted or unsubstituted nitrogen atoms, wherein the nitrogen substituent is alkyl as previously described. Exemplary alkylene groups include methylene (—$CH_2$—), ethylene (—$CH_2$—$CH_2$—), propylene (—$(CH_2)_3$—), cyclohexylene (—$C_6H_{10}$—), —CH=CH—CH=CH—, —CH=CH—$CH_2$—, —$(CF_2)_n(CH_2)_m$—, wherein n is an integer from about 1 to about 50 and m is an integer from 0 to about 50, —$(CH_2)_n$—N(R)—$(CH_2)_m$—, wherein each of m and n is independently an integer from 0 to about 50 and R is hydrogen or alkyl, methylenedioxy (—O—$CH_2$—O—) and ethylenedioxy (—O—$(CH_2)_2$—O—). An alkylene group can have about 2 to about 3 carbon atoms and can further have 6–50 carbons.

"Halo" or "halide" refers to fluoride, chloride, bromide or iodide.

"Vesicle" or "vesicular species" refers to a spherical entity that is characterized by the presence of an internal void. Preferred vesicles or vesicular species are formulated from lipids, including the lipid compounds of the present invention. In any given vesicle or vesicular species, the lipids can be in the form of a monolayer or bilayer, and the mono- or bilayer lipids can be used to form one or more mono- or bilayers. In the case of more than one mono- or bilayer, the mono- or bilayers are generally concentric. The lipid vesicles or vesicular species include such entities commonly referred to as liposomes, micelles and the like. Thus, the lipids can be used to form a unilamellar vesicle (comprising one monolayer or bilayer), an oligolamellar vesicle (comprising about two or about three monolayers or bilayers) or a multilamellar vesicle (comprising more than about three monolayers or bilayers). The internal void of the vesicles are generally filled with a liquid, including, for example, an aqueous liquid, a gas, a gaseous precursor, and/or a solid material, including, for example, an active agent.

"Liposome" refers to a generally spherical cluster or aggregate of amphipathic compounds, including lipid compounds, typically in the form of one or more concentric layers, for example, bilayers. A liposome comprising a carbohydrate-based phospholipid compound of the present invention is also referred to herein as a "carbohydrosome".

"Emulsion" refers to a lipoidal mixture of two or more liquids and is generally in the form of a colloid. The lipids can be heterogeneously dispersed throughout the emulsion. Alternatively, the lipids can be aggregated in the form of, for example, clusters or layers, including mono- or bilayers.

"Suspension" refers to a mixture of finely divided colloidal particles floating in a liquid.

"Hexagonal phase structure" refers to a generally tubular aggregation of lipids in liquid media, for example, aqueous media, in which the hydrophilic portion(s) of the lipids generally face inwardly in association with a liquid environment inside the tube. The hydrophobic portion(s) of the lipids generally radiate outwardly and the complex assumes the shape of a hexagonal tube. A plurality of tubes is generally packed together in the hexagonal phase structure.

"Active agent" refers to a substance that is capable of exerting an effect in an environment, setting, formulation, etc, in which it is placed. Representative active agents include bioactive agents as defined below and also include but are not limited to active agents typically employed in preparing cosmetics (including carriers), fragrances and perfumes, paints, semiconductor materials (e.g. a conductive material), food additives (e.g. flavorings), and dyes (e.g. the dyes themselves).

"Bioactive agent" refers to an active agent that is capable of exerting a biological effect in vitro and/or in vivo. The biological effect is preferably therapeutic in nature. As used herein, "bioactive agent" refers also to substances that are used in connection with an application that is diagnostic in nature, such as in methods for diagnosing the presence or absence of a disease in a patient. The bioactive agents can be neutral or positively or negatively charged. Preferably, the bioactive agents are negatively charged. Examples of suitable bioactive agents include pharmaceuticals and drugs, cells, gases and gaseous precursors (e.g. $O_2$), synthetic organic molecules, proteins, vitamins, steroids, polyanions, nucleosides, nucleotides, polynucleotides and diagnostic agents, such as contrast agents for use in connection with magnetic resonance imaging, ultrasound or computed tomography of a patient.

"Anionic group" refers to a group that is negatively charged. Preferred anionic groups include phosphate ($PO_4^-$) groups.

"Cationic group" refers to a group that is positively charged. Preferred cationic groups include ammonium ions ($NH_4^+$).

"Zwitterionic group" refers to a group that possesses both a positive and a negative charge.

"Genetic material" refers generally to nucleotides and polynucleotides, including deoxyribonucleic acid (DNA) and ribonucleic acid (RNA). The genetic material can be made by synthetic chemical methodology known to one of ordinary skill in the art, or by the use of recombinant technology, or by a combination of the two. The DNA and RNA can optionally comprise unnatural nucleotides and can be single or double stranded. "Genetic material" refers also to sense and anti-sense DNA and RNA, that is, a nucleotide sequence that is complementary to a specific sequence of nucleotides in DNA and/or RNA.

"Pharmaceutical" or "drug" refers to any therapeutic or prophylactic agent that is used in the prevention, diagnosis, alleviation, treatment or cure of a malady, affliction, disease or injury in a patient. Therapeutically useful polynucleotides and polypeptides are included within the definition of drug.

"In combination with" refers to the incorporation of a active (preferably a bioactive agent) with a lipid compound of the present invention. The lipid compound can be combined with the active agent in any of a variety of different ways. For example, when the lipid compound is in the form of a vesicle or a vesicular composition, the active agent can be entrapped within the internal void of the vesicle. The active agent can also be integrated within the layer(s) or wall(s) of the vesicle, for example, by being interspersed among lipids that are contained within the vesicular layer(s) or wall(s). In addition, the active agent can be located on the surface of a vesicle. In this case, the active agent can interact chemically with the surface of the vesicle and remain substantially adhered thereto. Such interaction can take the form of, for example, electrostatic interactions, hydrogen bonding, van der Waal's forces or covalent bonding. Alternatively, or in addition to, the active agent can interact with the surface of the vesicle in a limited manner. Such limited interaction would permit migration of the active agent, for example, from the surface of a first vesicle to the surface of a second vesicle.

"Intracellular" or "intracellularly" refers to the area within the plasma membrane of a cell, including the protoplasm, cytoplasm and/or nucleoplasm. "Intracellular delivery" refers to the delivery of a bioactive agent into the area within the plasma membrane of a cell.

"Cell" refers to any one of the minute protoplasmic masses that make up organized tissue, comprising a mass of protoplasm surrounded by a membrane, including nucleated and unnucleated cells and organelles.

"Immune competence" refers to the ability of the immune system to protect against pathogens or infectious agents.

"Solvent" refers to any liquid carrier that can be used to dissolve, suspend, or emulsify a compound of the present invention or to otherwise provide a compound of the present invention a medium in which to form a supramolecular structure. The term "solvent" can thus encompass a solution, a suspension and an emulsion.

II. General Considerations

In aqueous solution, phospholipids self-assemble into spherical self-closed lipid bilayer structures known as vesicles or liposomes. This state exists because of the amphiphilic nature of the phospholipid; the interactions of the molecule with its environment are directly related to the extent and nature of the hydrophobic and hydrophilic moieties of the phospholipid molecule. The geometry of the phospholipid molecule is important for determining structures that form in solution. Israelachvili, J. N. *Intermolecular and Surface Forces*; Academic Press Inc.: San Diego, Calif., United States of America, 1992. Phospholipids with short (<6 carbons) hydrocarbon chains are wedge shaped and typically form micelle-like structures. With an increase in hydrocarbon chain length (6–50 carbons), a more cylindrical geometry is obtained, and supramolecular structures such as bilayers, helixes and tubules, are formed.

When a single bilayer exists, the liposomes are called unilamellar. Multilamellar vesicles comprise many concentric vesicles much like an onion and can range in size over three orders of magnitude (10 nm to 10 mm). Needham, D.; Lasic, D. D. *Chem. Rev.* 1995, 95, 2601. The most common lipids in cell membranes are glycerol-based phospholipids. Hanahan, D. J. A Guide to Phospholipid Chemistry; Oxford University Press: New York, N.Y., United States of America, 1997. Phosphoglycerides have a glycerol backbone, two ester linked hydrophobic hydrocarbon chains as tail groups and a polar head group, which is often a choline group. Some of the more common head groups found in nature are the choline, ethanolamine, serine, inositol, and phosphatidic acid head groups. Ethanolamine is a common head group similar to the choline head group; however, it has a terminal —$NH_3^+$ instead of a terminal —$N(CH_3)_3^+$.

The lengths and degree of unsaturation of the tails of a phospholipid compound can also be modified, with the most common lengths of the tails ranging between 12 and 24 carbons and the most common site of unsaturation being at the C-9 position. In addition to varying the head group and the size of the tail group, the linkages attaching the tails to the backbone can be altered, with the ester linkage being the most prevalent. To a lesser extent, 'ether linked' phosphatidyl phospholipids, or 'plasmalogens' are also found in nature. The 'ether linked' phosphatidyl phospholipids are similar to ester linked phosphatidyl phospholipids in many ways except that an ether linkage replaces the ester linkage. Additionally, amide linkages, found in ceramides (sphingosines) are also present in naturally occurring phospholipids. Although the head groups, tail groups and linkages used to join these groups to the backbone of naturally occurring and synthetically prepared phospholipids vary considerably, the three carbon glycerol group is highly conserved. For example, the sphingosine ($CH_3(CH_2)_{12}$ CH—CH—HCOH—HCNH$_2$—CH$_2$OH) backbone is often considered to be a separate backbone. However, it maintains the three carbon unit glycerol backbone with an amide substituted as the linker for one chain (sn-2) and an alkene branching from the other (sn-1) as seen in sphingomyelin.

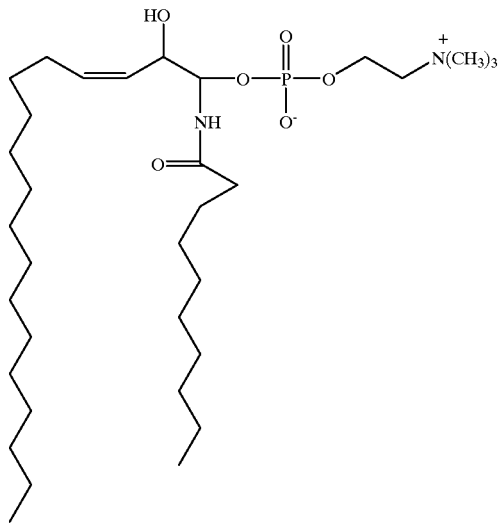

Sphingomyelin

In marked contrast, a preferred embodiment of the present invention comprises a novel class of phospholipids that possess a carbohydrate as the backbone.

III. Compounds

This present invention pertains to a unique class of lipids where the glycerol backbone is replaced with a carbohydrate. Zwitterionic, anionic, and cationic carbohydrate-based lipids/phospholipids were synthesized and characterized, and novel functionalities were observed. For example, it was observed that in an appropriate solvent, the novel compounds of the present invention self-assemble into supramolecular structures. Additionally, the pH dependent thermotropic behavior of synthetic carbohydrate-based phospholipids is characterized herein.

In one embodiment a phospholipid compound of the present invention comprises a hydrophilic head group, a lipophilic tail group, a carbohydrate backbone, and linker moieties between the head group and backbone and between the tail group and backbone, respectively. Representative head groups include but are not limited to choline, ethanolamine, serine, inositol, and phosphatidic acid head groups. Representative tail groups are set forth in as $R^1$, $R^2$ and $R^3$ in the definition of Formula (I) presented below, and can thus include but are not limited to lauroyl, myristoyl and arachadonyl groups, as well as other alkyl, alkenyl, and alkynl groups, and halo-substituted versions thereof. Representative linkers include but are not limited to carbonate, sulfate, phosphate, silane, ester, ether, amide, amine, urea, urethane, and thio moieties based thereon (e.g. thiol, thioesters, thioethers, thiourethane, thiourea and the like).

A preferred carbohydrate comprises a five (5)-carbon aldose or ketose, and more preferably the carbohydrate is ribose. Indeed, any carbohydrate (e.g. aldose or ketose) having 5 or more carbons (preferably 5, 6, 7, or 8 carbons) can be employed in the present inventive compound. Representative sugars thus also include but are not limited to arabinose, xylose, lxyose, glucose, mannose, galactose, ribulose, fructose and xylulose. The carbohydrate backbone can comprise a ring structure, and preferably comprises a furan-like 5-member ring, such as a cyclic hemiacetal furan ring structure, or a pyran-like 6-member ring, such as a cyclic hemiacetal pyran ring. The ring structure can be heterocyclic, and can thus have N, O or S in the ring.

Additionally, each of the carbons in the carbohydrate backbone preferably comprises a chiral or stereochemical center. Thus, R and S; (+) and (−); (α) and (β); and L and D carbohydrate backbones are within the scope of the present inventive compounds.

In a preferred embodiment a lipid compound of the present invention comprises:

Formula (I),

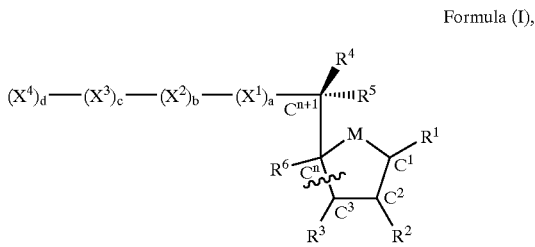

where each carbon of $C^{n+1}$ and $C^1$ to $C^n$ is a stereochemical center; each carbon of $C^1$ to $C^n$ is a member of a heterocyclic ring containing M; n=4, 5, 6 or 7; $R^1$, $R^2$, $R^3$, $R^4$, $R^5$ and $R^6$ are the same or different, and are selected from the group consisting of H, OH, amine, thiol, methoxy, straight or branched chain ester of 6–50 carbon atoms, straight or branched chain silane of 6–50 carbon atoms, straight or branched chain amide of 6–50 carbon atoms, straight or branched chain urea of 6–50 carbon atoms, straight or branched chain urethane of 6–50 carbon atoms, straight or branched chain carbonate of 6–50 carbon atoms, straight or branched chain sulfate of 6–50 carbon atoms, straight or branched chain thiol-urethane of 6–50 carbon atoms, straight or branched chain phosphate of 6–50 carbon atoms, straight or branched chain amine of 6–50 carbon atoms, straight or branched chain thio-urea of 6–50 carbon atoms, straight or branched chain thio-ether of 6–50 carbon atoms, straight or branched chain thio-ester of 6–50 carbon atoms, straight or branched chain ether of 6–50 carbon atoms, and any combination thereof, wherein the chain is fully saturated, fully unsaturated or any combination thereof; M and $X^1$ the same or different and are O, S, or N—$R^7$, wherein $R^7$ is H, a lower alkane, a chain as recited for $R^1$, $R^2$, or $R^3$, Se or any isoelectronic species of oxygen and a=0, 1, 2, 3, 4, 5, 6, 7, 8, 9, or 10; $X^2$ is phosphonate, phosphate, boronophosphate, thio-phosphate, or selenophosphate and b is 0, 1, 2, 3, 4, 5, 6, 7, 8, 9 or 10; $X^3$=methylene or a monomer selected from the group consisting of an ether, an ester, an amine, acrylic acid, amino acid, a nucleic acid, or a monosaccharide, and c=0, 1, 2, 3, 4, 5, 6, 7, 8, 9, 10, 11, 12, 13, 14, 15, 16, 17, 18, 19, or 20; and $X^4$=hydroxyl, N-succinyl derivative, a monomer selected from the group consisting of an amine, an ether, an ester, an amino acid, monosaccharide, and a nucleic acid, N—$(R^8)_e$ where $R^8$ is hydrogen or methylene chain of 1–20 carbons, or cyclic forms thereof and d=0, 1, 2, 3, 4, 5, 6, 7, 8, 9, or 10 and e=1, 2 or 3.

Thus, the ring containing M comprises a heterocyclic ring that can have 5 members (i.e., 4 carbons), 6 members (i.e., 5 carbons), 7 members (i.e., 6 carbons), or 8 members (i.e., 7 carbons).

Optionally, $X^1$, $R^1$, $R^2$, $R^3$, $R^4$, $R^5$ and $R^6$ can also further comprise an imine, glycolic acid, phosphate, thio-ester, thiol, thio-urethane, purines, pyrimidines, ether, thio-ether, ester or lactic acid. In this case, $X^1$ can further comprise a moiety such as polyethylene glycol or any other desired head group.

Optionally, the chains of $R^1$–$R^7$ are the same or different and are alkanes, alkenes, alkynes or halo-substituted version thereof, wherein halo is F, I, Cl, or Br. The chains of $R^1$–$R^7$ can also be or be substituted by a polyether (e.g polyethylene glycol-PEG), polyester (e.g. PLA, PGA), polyamine (e.g. PMMA), polyacrylic acid, polyamino acid, polynucleic acid and polysaccharides that are of molecular weight ranging from 200–1,000,000. In this case the chains of $R^1$–$R^7$ can comprise 1 or more photopolymerizable group.

The chains of $R^1$–$R^7$ can also be the same or different and terminate in an amine, thiol, amide, phosphate, sulphate, hydroxide or —SeH. Additionally, the chains of $R^1$–$R^7$ can be the same or different and can comprise a chain length of 10–24 carbon atoms. $(X^1)_a$—$(X^2)_b$—$(X^3)_c$—$(X^4)_d$ can also replace or substitute 1 or more of $R^1$, $R^2$, or $R^3$.

An antibody, a nucleotide, a nucleoside, an oligonucleotide, a polypeptide, a carbohydrate, a contrast agent, ligand, other bioactive agent, or any combination thereof can be attached to one of $R^1$, $R^2$, $R^3$, $X^1$, $X^2$, $X^3$, $X^4$, $R^4$, $R^5$ and $R^6$, or a combination thereof. The contrast agent can comprise a tomography agent or a magnetic resonance imaging agent, and can include particularly an iodated compound attached for X-ray imaging. The bioactive agent can comprise an antibacterial, anticancer, anti-inflammatory, or antiviral. The carbohydrate can comprise mannose or sialic acid.

Preferred zwitterionic carbohydrate-based phospholipids include but are not limited to bis-(2,3-lauroyl)-1-methoxy-5-(phosphocholine)-ribose (DLRPC), bis-(2, 3-myristoyl)-1-methoxy-5-(phosphocholine)-ribose (DMRPC) and bis-(2,3-arachadonyl)-1-methoxy-5-(phosphocholine)-ribose (DARPC). Preferred anionic carbohydrate-based phospholipids include but are not limited to bis-(2,3-lauroyl)-1-methoxy-5-ribo-phosphatidic acid (DLRPA). Preferred cationic carbohydrate-based phospholipids include but are not limited to 1-methoxy-2,3-dilauroyl-ribo-5-lysine (DLR-Lys).

IV. Supramolecular Structures

A supramolecular structure composition is also provided in accordance with the present invention. In a preferred embodiment, the composition comprises a compound of Formula (I). In accordance with the present invention it has been observed for the first time that a supramolecular structure comprising a compound of the present invention can self assemble into any of a variety of structures, including but not limited to a vesicle, a liposome, helix, disc, tube, fiber, torus, hexagonal phase, micelle, gel phase, reverse micelle, microemulsion, emulsion or combinations thereof. In the case of a liposome, the liposome is preferably multilamellar, single lamellar, or giant.

With respect to a supramolecular structure composition of the present invention comprising a compound of the Formula (I), the composition can further comprise one or more functional groups attached together either off of $C^1$ or $C^n$ in some way in order to form compounds similar to geminal lipids. A supramolecular structure composition of the present invention can further comprise one or more tail groups (e.g. $R^1$, $R^2$, or $R^3$ in Formula (I)) attached in a cyclical fashion to another lipid of any composition, such as in a bolalipid.

Optionally, the supramolecular structure composition is formed from a combination of a compound of Formula (I) with from 0.1–99.9% (by weight) of another material. In this embodiment, the inventive composition can thus comprise 5, 10, 20, 25, 50, or 75% compound of Formula (I) with the corresponding weight percent of another material, i.e. 95, 90, 80, 75, 50 and 25%, and vice versa. Representative, non-limiting other materials include conventional lipids, such as DPPC, and PEGylated DPPC; other fatty acids;

cholesterol; fluorescently labeled phospholipids; ether lipids, sphingolipids; phospholipids such as dimyristyl phosphocholine (DMPC); nucleic acids (e.g. DNA and other genetic material); amino acids and proteins; surfactants; and combinations thereof. Representative formulations are also set forth in the Examples. Indeed, in selecting substituents for the compound of Formula (I) or otherwise preparing or modifying a supramolecular structure composition of the present invention, substituents and materials can be chosen so that the compositions destabilize in acidic, basic, or neutral environments and/or destabilize in cold, warm, or ultrasonic environments.

The supramolecular structure can further comprise an interior space. The interior space can capture or encapsulate air or another desired gas, gaseous precursor, or mixture thereof. Representative gases include but are not limited to $N_2$, $O_2$, $CO_2$, NO, and $C_fF_{2f+1}$, where f=1, 2, 3, 4, 5 or 6. Representative fluorocarbons thus include but are not limited to perfluoromethane, perfluoroethane, perfluoropropane, perfluorobutane, perfluorocyclobutane, perfluoropentane, perfluorohexane and mixtures thereof.

The interior space can also encapsulate an aqueous solution. Representative aqueous solutions include but are not limited to water, buffered aqueous media, saline, buffered saline, solutions of amino acids, solutions of sugars, solutions of vitamins, solutions of carbohydrates and combinations of any two or more thereof.

The interior space can also encapsulate a non-aqueous liquid. Representative non-aqueous liquids include but are not limited to soybean oil; mineral oil; corn oil; rapeseed oil; coconut oil; olive oil; saflower oil; cottonseed oil; aliphatic; cycloaliphatic or aromatic hydrocarbons having 4–30 carbon atoms; aliphatic or aromatic alcohols having 2–30 carbon atoms; aliphatic or aromatic esters having 2–30 carbon atoms; alkyl; aryl or cyclic ethers having 2–30 carbon atoms; alkyl or aryl halides having 1–30 carbon atoms and having one or more halogen substituents where halogen is F, Cl, Br, or I; ketones having 3–30 carbon atoms; polyalkylene glycol; and combinations of any two or more thereof.

The supramolecular structure composition can further comprise a solid particle. Optionally, the solid particle is encapsulated in the interior space. However, the solid particle can be conjugated or otherwise in combination with the supramolecular structure. The solid particle can further comprise an active agent. Preferably, the solid particle further comprises a bioactive agent. Optionally, the solid particle can further comprise a phospholipid, a nucleic acid, a polynucleic acid, an amino acid, a protein, a surfactant or combinations thereof.

A supramolecular structure composition of the present invention can be adapted for delivering pharmaceuticals or for obtaining in vivo medical diagnostic images. A supramolecular structure composition of the present invention can also be adapted for the delivery of paints, dyes, fragrances and cosmetics; for the delivery of $O_2$ and other gases in vivo; for use in cleaning systems; for use in sensors, and for use in a semiconductor.

Thus, a process for preparing a supramolecular structure composition suitable for use in carrying an active agent is provided in accordance with the present invention. In a preferred embodiment, the process comprises combining together an active agent and a supramolecular structure composition that comprises a lipid compound of Formula (I). Optionally, the supramolecular structure formulation is lyophilized. Additionally, the supramolecular structure combination can be a micelle, a vesicle, a liposome, or mixtures thereof. The active agent can be entrapped within the interior space of the supramolecular structure.

A process for the preparation of a supramolecular structure composition for the intracellular delivery of a bioactive agent is also provided in accordance with the present invention. In a preferred embodiment, the process comprises combining together a bioactive agent and a supramolecular structure composition that comprises a phospholipid compound of Formula (I). Optionally, the supramolecular structure formulation is lyophilized. Additionally, the supramolecular structure combination can be a micelle, a vesicle, a liposome, or mixtures thereof. The bioactive agent can be entrapping within the interior space of the supramolecular structure. In a more preferred embodiment, the bioactive agent comprises genetic material.

A carbohydrosome of the present invention can also be prepared utilizing techniques similar to those employed in the art for conventional liposome preparation. Such conventional techniques are referred to in WO92/21017 (Unger) and by Papahadjopolous in Ann Rep. Med. Chem. 14: 250–260 (1979) and include reverse evaporation, freeze-thaw, detergent dialysis, homogenization, sonication, microemulsification and spontaneous formation upon hydration of a dry lipid film. In a preferred embodiment, a film of the lipid is deposited on a glass coverslip and then incubated in a sucrose solution for a predetermined time, such as 12 hours. A thin film of lipid is then deposited on the inside of a round bottom flask and then rehydrated at a temperature above its phase transition temperature ($T_m$). Then, the hydrated lipids are sonicated in order to form carbohydrosomes.

By way of additional example, for the X-ray diffraction samples disclosed below in the Examples, multilamellar carbohydrosomes were prepared by rehydrating the lipid powder in excess water and vortexing the mixture between cycling the temperature above and below the lipid's $T_m$. Carbohydrosomes were also prepared by simply rehydrating the lipid in excess water or buffer and heating above the $T_m$. When carbohydrosomes of a specific size were desired as in the leakage assays described in the Examples, a high-pressure extrusion technique utilizing filters was employed.

V. Applications

One of the more important abilities of liposomes is that substances such as pharmaceutical agents can be encapsulated inside the vesicles, providing both protection from the immune system and enzymatic degradation as well as acting as a vehicle for the carried compound(s), thereby providing sustained drug release. See U.S. Pat. No. 4,235,871 to Papahadjopoulos and Szoka Jr.; Honma, Y., et al., Cancer. Chemother. Pharmacol. 1983, 11, 73–76.) Liposomal drug formulations improve the pharmacokinetics of extremely toxic drugs by releasing the drug in a time dependant manner closer to ideal zero order kinetic delivery and less like a first order injection. This formulation increases the amount of time the body is in the therapeutic window of the drug while at the same time decreases the time spent above the toxic threshold, therefore increasing the drug's therapeutic index. This pharmacokinetic characteristic is extremely important for delivery of both highly toxic drugs as well as drugs which have short in-vivo half-lives. The net effect is an increase in use of such drugs by improving dosing regimens and therefore improving compliance. For example, liposomal formulations decrease the toxicity and necessary doses of highly toxic drugs such as the anti-neoplastics (doxorubicin), and anti-fungals (amphotericin B); both are currently marketed as liposomal formulations. U.S. Pat. No. 5,077,056 to Bally et al.; U.S. Pat. No. 4,766,046 to Abra et al. In addition, liposomes can be conjugated to various ligands such as antibodies, which help to target the liposome to specific cells. The carbohydrate based lipid compounds of the present invention are thus used in the preparation of liposomes for drug delivery.

Liposomal formulations are also used to deliver drugs such as steroids to the lungs in an effort to decrease adverse side effects as well as increase absorption. Suntres, Z. E.; Shek, P. N. *J. Drug Targeting* 1998, 6, 175–82. These formulations are often used to treat diseases where systemic absorption of the steroid is not desired such as interstitial lung diseases (ILD), chronic obstructive pulmonary disease (COPD), asthma as well as infections. (Deol, P.; et al., *Antimicrobial Agents & Chemotherapy* 1997, 41, 1211–1214.) Additionally, pH-sensitive liposomes have been investigated in order to improve drug delivery to cells. Nayer, R.; Schroit, A. *Biochemistry* 1985, 24, 5967–5971.) Liposomes have also been used in immunoassays for rapid screening of diseases, such as syphilis, hepatitis B, and mononucleosis. Litzenger, D.; Huang, L. *Biochem. Biophys. Acta.* 1992, 1113, 201–227. Other medical applications of liposomes include enzyme replacement therapy, cancer treatment, anti-microbial therapy, metal storage disease treatment, immunological adjuvants, and arthritis treatment. (Gregoriadis, G. *Liposomes*; Gregoriadis, G., Ed.; John Wright and Sons, Ltd.: Bristol, England, United Kingdom, 1979, pp 287–349.) Drug delivery through and to the skin is important medically for dermatological purposes. Delivery is improved by the lipophilic nature of phospholipids to improve absorption. Alcoholic aqueous gel-like phospholipids have also been used for topical preparations. U.S. Pat. No. 5,711,965 to Ghyczy et al.

Additional applications of liposomes include the following. Liposomes have been tested for oral delivery of insulin, as well as been used for artificial blood by encapsulation of oxygen carrying molecules such as hemoglobin or perfluorocarbons. Dapergolas, G.; Gregoriadis, G. *Lancet* 1976, Oct. 16, 824–827; Rudolph, A. S. *Encapsulation of Hemoglobin in Liposomes*; Rudolph, A. S., Ed.; Birkhauser: Boston, Mass., United States of America 1995. Phospholipids are also known to exhibit spermicidal activity. U.S. Pat. No. 5,215,976 to Fost.

Stealth liposomes, or sterically hindered liposomes, are constructed from modified phospholipids containing a long hydrophilic chain that forms a protective layer around the liposome, sterically hindering interactions between the immune system, therefore retarding uptake and destruction of the liposome and its contents. Needham, D.; Lasic, D. D. *Chem. Rev.* 1995, 95, 2601. A hydrophilic chain, typically polyethylene glycol, is attached to the head group of conventional phospholipids. A unique advantage of the preferred carbohydrate-based phospholipid of the present invention is that an additional site on the sugar which is not present in the glycerol based phospholipid can be used as the attachment site for the hydrophilic chain therefore eliminating the need to interfere with head group functionality.

Cationic liposomes have been used as vectors for gene therapy. U.S. Pat. No. 5,264,618 to Felgner, P. L. et al. The positive charge on the lipid interacts with the negative charge on DNA, facilitating transfection. Phospholipids can also be used in detergents, and emulsifiers, which are often used in foods and medicines. U.S. Pat. No. 5,328,628 to Hart et al.; U.S. Pat. No. 4,357,353 to Strauss et al.; U.S. Pat. No. 5,496,818 to Schaupp et al.

Gene therapy, defined as the introduction of nucleic acids into cells for the purpose of altering the course of a medical condition or disease, offers one of the most exciting prospects for the future of medicine. The final goal of gene therapy is to correct both acquired and inherited disorders by removing their origins or correcting the etiology. This correction can be accomplished by replacing, adding, or removing genes and gene therapy is discussed at length by Templeton and Lasic. Garnett, M. C. *Crit. Rev. Ther. Drug Carrier Sys.* 1999, 16, 147–207; Zhao, X. *The Application of Electronic Pulse Delivery in Gene Therapy: Progress and Perspectives*; Zhao, X., Ed.; American Chemical Society: Washington D.C., 1996, pp 63–71.

A major obstacle of gene therapy is lack of or low permeability of the cell membrane to highly charged macromolecules such as DNA. Scientists have developed numerous techniques for overcoming this hurdle such as electroporation, direct injection, viral transduction, calcium phosphate ($Ca_3(PO_4)_2$), and supramolecular (liposomal and polymeric) systems. (Garnett, M. C. *Crit. Rev. Ther. Drug Carrier Sys.* 1999, 16, 147–207; Haensler, J.; Szoka, F. A. Bioconj. *Chem.* 1993, 4, 372. Hanania, E. G., et al., *Amer. J. Med.* 1995, 99, 537–552; Yant, S. R., et al., *Nature Genetics* 2000, 25, 35–41. Currently, viral vectors exhibit the highest levels of gene transfer, resulting in their clinical trial use. (Huang, L.; Viroonchatapan, E. Introduction; Huang, L.; Viroonchatapan, E., Ed.; Academic Press: New York, 1999, pp 4–17.) Focus on non-viral gene carriers has emerged because of limiting factors of viral vectors such as immunogenicity, mutagenesis, loadable gene size limit, problematic industrial scale production and safety. Unfortunately, each of the non-viral vectors has shortcomings. For example, cationic phospholipids have been associated with high levels of toxicity, and $Ca_3(PO_4)_2$ mediated delivery suffers from poor reproducibility. Han, S., et al. *Molecular Therapy* 2000, 2, 302–317; Pack, D. W.; Putnam, D.; Langer, R. *Biotech. and Bioeng.* 2000, 67, 217–223; Porschke, D. *Biochemistry* 1984, 23, 4821; Farhood, H., et al., *Biochim. Biophys. Acta* 1995, 1235, 289–295; Lesney, M. S. *Modern Drug Discovery* 2000, 55–60.

Liposomes are used as imaging contrast agents. They can be used to encapsulate an imaging agent to facilitate magnetic resonance imaging (MRI), X-ray, positron emission tomography (PET) and ultrasonic imaging. For ultrasonic imaging, a gas or perfluorocarbon is encapsulated inside the liposome and then it is injected near the site that is to be imaged, such as the heart. The difference in density between the perfluorocarbon in the liposome and the rest of the body is readily apparent for imaging purposes. U.S. Pat. No. 5,049,389 to Ungar et al.; U.S. Pat. No. 5,456,901 to Ungar.

Thus, in accordance with the present invention, a method for delivery of a bioactive agent to a subject is provided. In a preferred embodiment, the method comprises administering to the subject a supramolecular structure composition that comprises a compound of Formula (I) and the bioactive agent, whereby delivery of the bioactive agent to the subject is accomplished.

In accordance with the present invention, a method for delivering intracellularly a bioactive agent is also provided. In a preferred embodiment, the method comprises contacting a cell with a supramolecular structure composition that comprises a compound of Formula (I) and the bioactive agent. Optionally, the cell comprises a cell in a warm-blooded vertebrate subject.

In accordance with the present invention, a method for drug delivery to a warm-blooded vertebrate having a medical condition that is ameliorated by treatment with the drug comprising administering to the warm-blooded vertebrate an effective amount of a composition that comprises a compound of Formula (i) and the drug; and observing amelioration of the medical condition.

The composition can be reconstituted from a lyophilized composition. Preferably, the composition is selected from the group consisting of micelles, liposomes and mixtures thereof. More preferably, the bioactive agent entrapped within the micelles or liposomes. As discussed above, the bioactive agent can comprises genetic material. Optionally, the genetic material is selected from the group consisting of polynucleotide, DNA, RNA, polypeptide and mixtures thereof.

The compositions of the present invention preferably comprise a pharmaceutical composition that includes a pharmaceutically acceptable carrier. Any suitable pharmaceutical formulation can be used to prepare the compositions for administration to a subject.

For example, suitable formulations can include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some preferred ingredients are SDS, for example in the range of 0.1 to 10 mg/ml, preferably about 2.0 mg/ml; and/or mannitol or another sugar, for example in the range of 10 to 100 mg/ml, preferably about 30 mg/ml; and/or phosphate-buffered saline (PBS).

It should be understood that in addition to the ingredients particularly mentioned above the formulations of this invention could include other agents conventional in the art having regard to the type of formulation in question. Of the possible formulations, sterile pyrogen-free aqueous and non-aqueous solutions are preferred.

Suitable methods for administration of a composition of the present invention include but are not limited to intravenous, subcutaneous, or intratumoral injection. Alternatively, the composition can be deposited at a site in need of treatment in any other manner, for example by spraying a composition comprising a bioactive agent within the pulmonary pathways. The particular mode of administering a therapeutic composition of the present invention depends on various factors, including the distribution and abundance of cells to be treated, the bioactive agent employed, and mechanisms for metabolism or removal of the composition from its site of administration.

The subject treated in the present invention in its many embodiments is desirably a human subject, although it is to be understood that the principles of the invention indicate that the invention is effective with respect to invertebrate and to all vertebrate species, including mammals, which are intended to be included in the term "subject". Moreover, a mammal is understood to include any mammalian species in which treatment or prevention of cancer or infectious diseases is desirable, particularly agricultural and domestic mammalian species.

The methods of the present invention are particularly useful in the treatment of warm-blooded vertebrates. Thus, the invention concerns mammals and birds.

More particularly, contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

The field of cosmetics also has found a use for phospholipids. Phospholipids are known to form asymmetric lamellar aggregates that penetrate through the horny layer of the skin, therefore increasing oxygen concentrations in the dermis. This increases metabolism, therefore improving skin growth and a healthy appearance. U.S. Pat. No. 5,643,601 to Gross et al. In addition, cosmetic emulsions made with phospholipids are used for lipstick and lip-gloss. U.S. Pat. No. 5,085,856 to Dunphy et al. Thus, the present invention provides a composition comprising a supramolecular structure composition of the present invention and a cosmetic carrier, such as those disclosed in U.S. Pat. No. 6,235,772, herein incorporated by reference.

Supramolecular structure compositions of the present invention also find application in cleaning compositions, dyes, petroleum products, electronics, semiconductors, composites, optics, and paints.

VI. Laboratory Examples

The following Examples have been included to illustrate modes of the invention. Certain aspects of the following Examples are described in terms of techniques and procedures found or contemplated by the present co-inventors to work well in the practice of the invention. These Examples illustrate standard laboratory practices of the co-inventors. In light of the present disclosure and the general level of skill in the art, those of skill will appreciate that the following Examples are intended to be exemplary only and that numerous changes, modification and alteration can be employed without departing from the scope of the invention.

Preparation of Carbohydrosomes Characterized in Examples

A carbohydrosome of the present invention was prepared utilizing techniques similar to those employed in the art for conventional liposome preparation. A film of the lipid was deposited on a glass coverslip and then incubated in a sucrose solution for 12 hours. A thin film of lipid was then deposited on the inside of a round bottom flask and then rehydrated at a temperature above its phase transition temperature ($T_m$). Then, the hydrated lipids were sonicated in order to form carbohydrosomes.

For the X-ray diffraction samples disclosed below in the Examples, multilamellar carbohydrosomes were prepared by rehydrating the lipid powder in excess water and vortexing the mixture between cycling the temperature above and below the lipid's $T_m$. Carbohydrosomes were also prepared by simply rehydrating the lipid in excess water or buffer and heating above the $T_m$. When carbohydrosomes of a specific size were desired as in the leakage assays described in the Examples, a high-pressure extrusion technique utilizing filters was employed.

EXAMPLE 1

Zwitterionic Phospholipid
Synthesis of Carbohydrate-Based Phospholipids DLRPC, DMRPC and DARPC

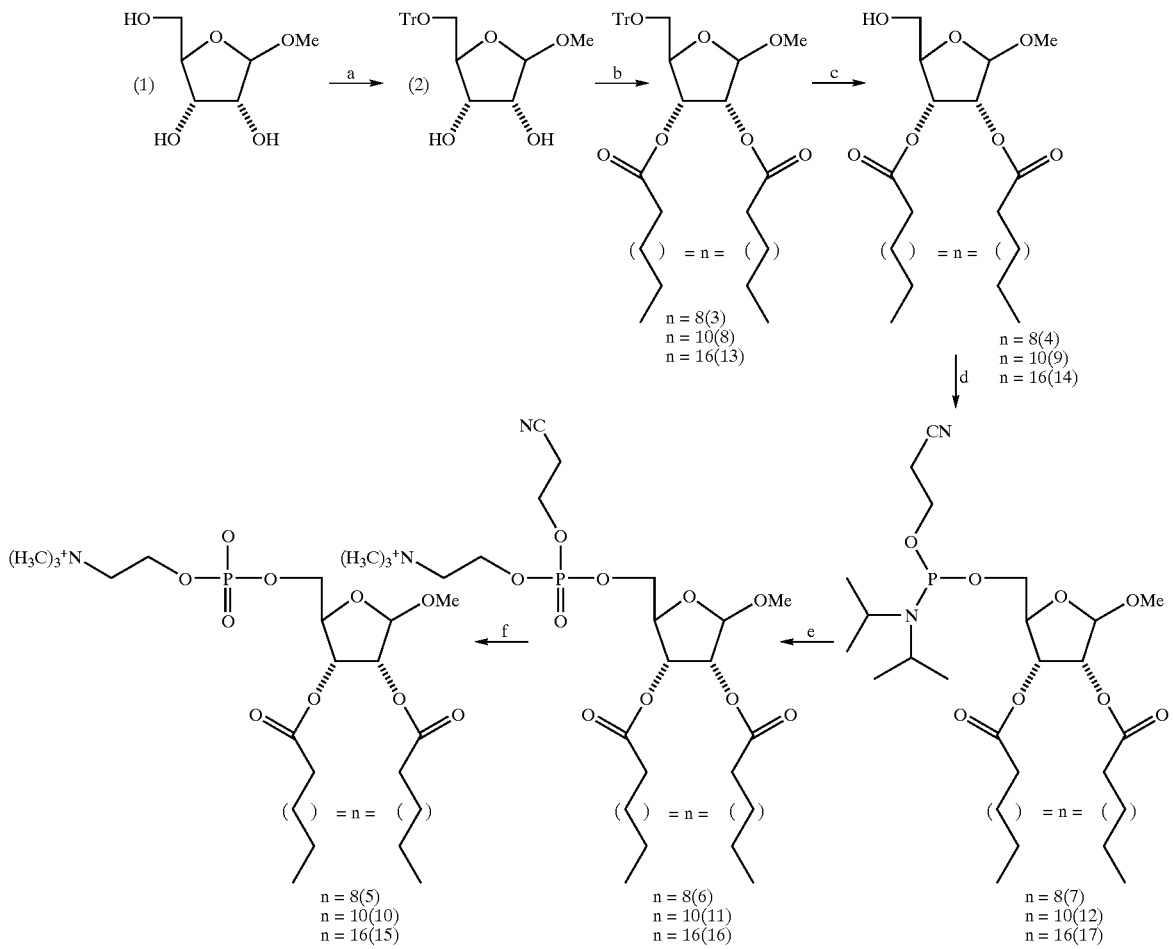

Scheme 1 a) TrCl, $C_5H_5N$, 3 hrs., 120° C., b) DCC, DMAP, lauric/myristic/arachadonic acid, DMF, 48 hrs., 60° C., c) acetic acid, $H_2O$, 12 hrs., 50° C., d)2-cyanoethyl diisopropyl-chlorophosphoramidte, DIPEA, $CH_2Cl_2$, 2 hrs., 22° C., e) tetrazole, choline chloride, $I_2$, ACN, 3 hrs., 22° C., f) TEA (aq), 3 hrs., 22° C.

Scheme 1—Synthetic Scheme for bis-(2,3-lauroyl)-1-methoxy-5-(phosphocholine)-ribose (DLRPC), bis-(2,3-myristoyl)-1-methoxy-5-(phosphocholine)-ribose (DMRPC) and bis-(2,3-arachadonyl)-1-methoxy-5-(phosphocholine)-ribose (DARPC)

Methyl-2,3-di-O-lauroyl-b-D-ribo-5-phosphocholine, 7 (DLRPC), methyl-2,3-di-O-myristoyl-b-D-ribo-5-phosphocholine, 12 (DMRPC) and methyl-2,3-di-O-arachadonyl-b-D-ribo-5-phosphocholine, 17 (DARPC) were synthesized as shown in Scheme 1. The first step involves protecting the primary hydroxide of 1 using trityl chloride. Purification of 2 is accomplished by silica gel column chromatography in 87% yield with an eluent of 3% methanol/chloroform. Next, a DCC coupling with DMAP and lauric/myristic/arachadonic acid in DMF affords compound 3, 8, or 13, respectively. These compounds are purified on a silica gel column with the eluent of 9/1 hexane/ethyl acetate, then immediately dissolved in aqueous acetic acid to remove the trityl protecting group. Compounds 4, 9, and 14 are subsequently purified by silica gel column chromatography (eluent 7/3 hexane/ethyl acetate) with an overall yield of 88%, 49%, and 36% from 2 to 4, 9, and 14 respectively. The synthesis of compound 5, 10, and 15 is accomplished by first reacting 4, 9, and 14 with 2-cyanoethyl diisopropylchlorophosphoramidite followed by addition of choline chloride in the presence of tetrazole. The phosphorous (III) compound is subsequently oxidized to phosphorous (V) by $I_2$.

Finally, the cyanoethyl protecting group of 6, 11, and 16 is removed by dissolving the mixture in 0.14 M (aq) TEA and stirring for 3 hours at room temperature. Compound 7 or 12 is isolated after alumina (65/25 chloroform/methanol-65/25/4 chloroform/methanol/$H_2O$), SEPHADEX™ G-10 size exclusion chromatography (50/50 chloroform/methanol), and reverse phase C-18 SEP PAK™ chromatography (10/90 methanol/chloroform). The overall yield for these three steps (d–f) is 33.5% and 22.4% respectively. Since 17 possesses long chains, its purification is slightly different; 17 is dissolved in benzene and the impurities are removed by filtration. The benzene solution is concentrated to a minimum before layering with MeOH and refrigerating overnight. The resulting precipitate is filtered from solution and purified using a G-10 size exclusion column in 50/50 $CHCl_3$/MeOH. Finally, a neutral alumina column (65/25 $CHCl_3$/MeOH-65/25/4 $CHCl_3$MeOH/$H_2O$) is used to isolate 17 in a 5.2% yield.

β-methoxy ribose 1 (0.82 g, 5.01 mmol) and trityl chloride (1.63 g, 5.83 mmol) were both dissolved in 100 mL dry pyridine and heated to 120° C. for 3 hours. The solvent was evaporated under high vacuum and the resultant oil dissolved in chloroform. The chloroform was washed with water, 0.5 N HCl and then again with water before being dried with $Na_2SO_4$.

Silica gel column chromatography was performed (0–3% methanol in chloroform) yielding (2) in an 87% yield (1.77 g, 4.40 mmol). 1H-NMR (CD3Cl, 400 MHz, ppm): Phenyl Protons, 7.19–7.6 (15H, m); H(2), 4.860 (1H, s); H(4), 4.232 (1H, dd, J=6.4 Hz, 4.8 Hz); H(5), 4.092 (1H, m); H(3), 4.0005 (1H, d, J=4.4 Hz); H(1) 3.321 (3H, s); H(6) 3.246 (2H, m); H(2) 4.860 (1H, s). 1H-NMR data confirmed by comparison with literature values. (Kawana, M.; Kuzuhara, H.; Emoto, S. *Bull. Chem. Soc. Jpn.* 1981, 54, 1492–1504.)

bis-(2,3-lauroyl)-1-methoxy-5-hydroxy-ribose, 4

A solution of 2 (1.12 g, 6.80 mmol), lauric acid (4.36 g, 21.75 mmol), DMAP (2.66 g, 21.75 mmol), and DCC (4.49 g, 21.75 mmol) were dissolved in 175 mL dry DMF and stirred at 40° C. for 48 hours. Next, 2 mL of 5% acetic acid was added and the reaction was stirred for an additional 15 minutes before removing the solvent via high vacuum. The resultant oil was dissolved in chloroform and washed with 0.5 N HCl, 5% $NaHCO_3$, and water and then dried with $Na_2SO_4$ before evaporation via high vacuum. Silica gel column chromatography (10% ethyl acetate in hexane) yielded crude 3, which was dissolved in 150 mL of aqueous acetic acid and heated at 50° C. for 12 hours. The solvent was removed via high vacuum and the oil azeotroped with toluene. Silica gel chromatography (10–30% ethyl acetate in hexane) afforded 4 in 41% yield (1.47 g, 2.78 mmol). $^1$H-NMR (CD$_3$Cl, 400 MHz, ppm): H(3), 5.337 (1H, t, J=5.6 Hz); H(4), 5.231 (1H, d, J=4.8 Hz); H(2), 4.882 (1H, s); H(5), 4.195 (1H, m); H(6), 3.859 (2H, m); H(1), 3.410 (3H, s); H( ), 2.329 (m); H(β), 1.607 (m); H(γ), 1.256 (m); H(10), 0.859 (t, J=7.2 Hz). FAB Mass Spectrometry ((M−H)+ theoretical=528.4/observed=527.4)

bis-(2,3-lauroyl)-1-methoxy-5-(phosphocholine)-ribose, 7

2-cyanoethyl diisopropylchlorophosphoramidite (0.75 g, 3.35 mmol) was added dropwise to a 0° C. solution of 4 (1.47 g, 2.79 mmol) and N,N-diisopropylethylamine (0.75 mL, 3.90 mmol) in 50 mL of dry methylene chloride. The resultant was stirred at 21° C. for 3 hours, and then 1 mL of 30 methanol was added. The solvent was removed via high vacuum after ½ hour of stirring. The resultant oil 5 was dissolved in $CH_2Cl_2$ and washed with 5% $NaHCO_3$ and water before being dried with $Na_2SO_4$. Choline chloride (0.47 g, 3.35 mmol) was added to the flask and subsequently dried with 5 under high vacuum overnight. Tetrazole (0.25 g, 3.62 mmol) was next added with 100 mL dry acetonitrile and the reaction mixture was stirred for 7 hours. An oxidizing solution of 0.1 M $I_2$ in THF/Pyr/$H_2O$ (approximately 20 mL) was added until $I_2$ remained. The solvent was removed via high vacuum yielding crude 6 (4.50 g). To remove the cyanoethyl protecting group, 6 (0.34 g) was dissolved in 43 mL of 0.14 M (aq) TEA and stirred for 3 hours. The TEA was removed via high vacuum and the remaining water was removed through lyophilization.

Purification of 7 was achieved through alumina chromatography (65/25 chloroform/methanol-65/25/4 chloroform/methanol/$H_2O$), SEPHADEX™ G-10 chromatography size exclusion chromatography (50/50 chloroform/methanol), and finally C-18 Sep Pak™ chromatography (10/90 methanol/chloroform). A white solid 7 was obtained in 33.5% for the last three steps (45.4 mg). COSY and HMQC spectrum were performed in order to assign the peaks of the $^1$H-NMR. $^1$H-NMR (CD$_3$CN, 400 MHz, ppm): H(3), 5.205 (1H, t, J=5.40 Hz); H(4), 5.122 (1H, dd, J=4.80 Hz); H(2), 4.868 (1H, d, J=1.6 Hz); H(5), 4.173 (1H, m); H(7), 4.173 (1H, m); H(6), 3.848 (1H, m); H(6), 3.773 (1H, m); H(8), 3.492 (2H, t, J=4.4 Hz); H(1), 3.345 (3H, s); H(9), 3.144 (9H, s); H(α), 2.284 (4H, m); H(β), 1.548 (4H, m); H(γ), 1.266 (m); H(10), 0.872 (t, 6.40 Hz), $^{13}$C-NMR (CD$_3$CN, 500 MHz, ppm): C(11), 173.54; C(12), 173.50; C(4), 75.15; C(3), 72.53; C(2), 107.13; C(5), 81.91; C(7), 59.97; C(6), 59.53; C(8), 67.48; C(1), 55.44; C(9), 54.80; C(a)34.32; C(b), 25.401; C(10), 12.21; C(γ), 1.27, 1.28, 1.29; ($^{31}$P-NMR=0.067 ppm), High Resolution FAB Mass Spectrometry((MH)+theoretical=694.4659/observed= 694.4653)

bis-(2,3-myristoyl)-1-methoxy-5-hydroxy-ribose, 9

A DCC (4.93 g, 23.86 mmol) coupling of 2 (1.22 g, 7.46 mmol) with DMAP (2.92 g, 23.86 mmol) and myristic acid (5.45 g, 23.86 mmol) stirred in 150 mL DMF for 48 hours at 60° C. was used to obtain compound 8. The reaction mixture was quenched with 15 mL 5% acetic acid before removing solvent under high vacuum at 50° C. The resultant mixture was purified on a silica gel column with the eluent of 9/1 Hex/EtAc and then immediately dissolved in aqueous acetic acid and stirred at 50° C. for 12 hours. Product 9 was subsequently purified with a silica gel column (eluent 7/3 Hex/EtAc) to provide 9 (2.12 g, 3.63 mmol) in an overall yield of 49% from 2 to 9.

bis-(2,3-myristoyl)-1-methoxy-5-(phosphocholine)-ribose, 12

The synthesis of compound 10 was achieved by reacting 9 (0.64 g, 1.09 mmol) with 2-cyanoethyl diisopropylchlorophosphoramidite (0.37 mL, 1.64 mmol) at 0° C. in the presence of N,N-diisopropyl ethylamine (0.33 mL, 1.86 mmol) in 60 mL dry $CH_2Cl_2$ and stirred for 2 hours at room temperature under $N_2$. This reaction mixture was quenched with 2 mL MeOH and then completely evaporated at room temperature under high vacuum. The mixture was dissolved in distilled $CH_2Cl_2$ and then washed with 5% $NaHCO_3$ and water before being dried with $Na_2SO_4$. Choline chloride (0.20 g, 1.42 mmol) was added to the reaction vessel and then dried by azeotroping two times with benzene before being dried under high vacuum overnight.

Next, the resultant mixture containing compound 10 was dissolved in 100 mL dry $CH_3CN$ before adding tetrazole (0.10 g, 1.42 mmol) and stirring for 5 hours. An oxidizing solution of 0.2 M $I_2$ in THF/Pyr/$H_2O$ was added with stirring until the solution remained yellow indicating that the reaction was fully oxidized, finally yielding compound 11. This mixture was again evaporated and azeotroped with benzene. To remove the cyanoethyl protecting group, the contents of the reaction vessel were dissolved in 0.134 M (aq) TEA and stirred for 3 hours at room temperature. After removing all the TEA with high vacuum, the water was removed by lyophilization. 12 was purified by alumina column chromatography (65/25 $CHCl_3$/MeOH-65/25/4 $CHCl_3$/MeOH/ $H_2O$), followed by SEPHADEX™ G-10 size exclusion chromatography (50/50 $CHCl_3$/MeOH), followed by C-18 SEP PAK™ chromatography (10/90 MeOH/$CHCl_3$).

This procedure provided pure 7 (0.18 g, 0.25 mmol) in a 22.4% yield for the last three steps d–f of scheme 1. $^1$H-NMR (CD$_3$CN, 400 MHz, ppm): H(4), 5.209 (1H, t, J=31.2 Hz); H(3), 5.120 (1H, dd, J=2.2 Hz); H(2), 4.870 (1H, d, J=0.8 Hz); H(5), 4.190 (1H, m); H(7), 4.190 (1H, m); H(6), 3.880 (1H, m); H(6), 3.801 (1H, m); H(8) 3.513 (2H, t, J=4.8 Hz); H(1), 3.344 (3H, s); H(9), 3.141 (9H, s); H(α), 2.282 (4H, m); H(β), 1.542 (4H, m); H(γ), 1.261 (m); H(10), 0.871 (t, 7.2 Hz); $^{13}$C-NMR(CD$_3$CN, 400 MHz, ppm): C(11), 173.62; C(12), 173.35; C(4), 75.12; C(3), 72.17; C(2), 107.15; C(5), 80.97; C(7), 60.40; C(6), 59.20; C(8), 67.10; C(1), 55.75; C(9), 54.89; C(α) 34.52; C(β), 25.51; C(10), 14.39 (FIG. 3); 31P-NMR (−0.595 ppm); High Resolution FAB Mass Spectrometry ((M−H+) theoretical=750.5285/observed=750.5255).

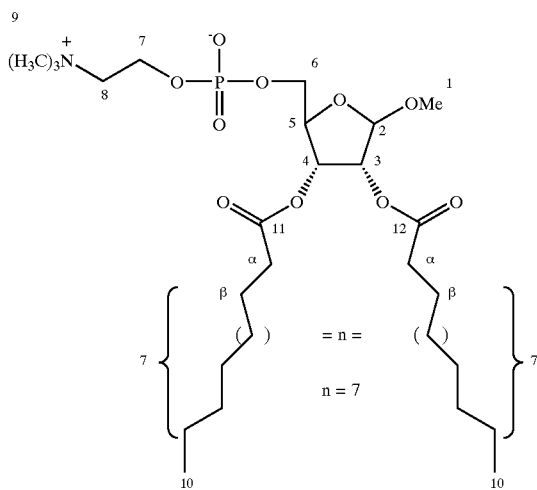

$^{13}$C-NMR Assignment for DMRPC bis-(2,3-arachadonyl)-1-methoxy-5-hydroxy-ribose, 14

Compound 2 (1.02 g, 6.20 mmol) was dissolved in 200 mL dry DMF with arachadonic acid (6.19 g, 19.81 mmol) and DMAP (2.42 g, 6.20 mmol) before adding DCC (4.09 g, 6.20 mmol) dropwise and stirring at 40° C. overnight. Next, 5 mL 5% acetic acid was added to the reaction vessel before filtering the white precipitate. The resultant solution was evaporated under high vacuum before being dissolved in CHCl$_3$ and washed with 0.5 N HCl, 5% NaHCO$_3$ and water. After drying with Na$_2$SO$_4$, the solution was rotoevaporated to dryness. Silica gel column purification (9/1 Hex/EtAc) was performed. The product was dissolved in aqueous acetic acid and stirred at 50° C. overnight to remove the trityl protecting group. The deprotected product 14 was purified by silica gel column chromatography (9/1 Hex/EtAc-7/3 Hex/EtAc) to provide 14 in a 36% yield (1.60 g).

bis-(2,3-arachadonyl)-1-methoxy-5-(phosphocholine)-ribose, 17

The dry alcohol 14 (1.18 g, 2.46 mmol) was dissolved in 45 mL dry CH$_2$Cl$_2$ before DIPEA (0.73 mL, 4.18 mmol) was added. The reaction vessel was then chilled to 0° C. before adding 2-cyanoethyl diisopropylchlorophosphoramidite (0.02 mL, 3.70 mmol). The reaction was stirred for 4 hours at 22° C. before being evaporated under high vacuum for 1.5 hours. The dried material was dissolved in CH$_2$Cl$_2$ from the still and then washed with 5% NaHCO$_3$ and H$_2$O before being dried with Na$_2$SO$_4$. Choline chloride (0.49 g, 3.20 mmol) was added to the flask before being azeotroped twice with toluene and put on high vacuum overnight at 45° C. The reaction mixture was dissolved in 94/6 CH$_3$CN/CH$_2$Cl$_2$ before adding tetrazole (0.22 g, 3.20 mmol) and stirred for 12 hours. Oxidation was performed using I2 in THF/Pyr/H$_2$O and stirred for 1 hour before evaporation under high vacuum. The resultant mixture was dissolved in 113 mL of H2O containing 2 mL of TEA and stirred for 3 hours. The solvent was then removed by lyophilization overnight.

In order to purify the product, the reaction mixture was dissolved in benzene and the impurities filtered out. The benzene solution was concentrated to a minimum before layering with MeOH and refrigerating overnight. The resulting product containing the precipitate was filtered from solution and purified using a G-10 size exclusion column in 50/50 CHCl$_3$/MeOH followed by a neutral alumina (70–230 mesh) column (65/25 CHCl$_3$/MeOH-65/25/4 CHCl$_3$/MeOH/H$_2$O). 0.12 g (5.2% yield) of product was obtained.

The product had an Rf=0.2 in 65/24/4 CH$_2$Cl$_2$/MeOH/H$_2$O by TLC. $^1$H-NMR (CD$_2$Cl$_2$/CD$_3$OD, 400 MHz, ppm): H(4), 5.276 (1H, t, J=5.6 Hz); H(3), 5.148 (1H, m); H(2), 4.870 (1H, m); H(5), 4.230 (1H, m); H(7), 4.230 (1H, m); H(6), 3.957 (1H, m); H(6), 3.909 (1H, m); H(8) 3.584 (2H, m); H(1), 3.330 (3H, s); H(9), 3.170 (9H, s); H(α), 2.275 (4H, m); H(β), 1.555 (4H, m); H(γ), 1.225 (m); H(10), 0.840 (t, 7.2 Hz); $^{13}$C-NMR (CD$_2$Cl$_2$/CD$_3$OD, 400 MHz, ppm): C(11), 173.43; C(12), 173.18; C(4), 74.83; C(3), 71.81; C(2), 106.64; C(5), 80.60; C(7), 62.73; C(6), 59.30; C(8), 67.11; C(1), 55.507; C(9), 54.72; C(α)34.32; C(β), 25.12; C(10), 14.18; $^{31}$P-NMR (CD$_2$Cl$_2$/CD$_3$OD, 400 MHz, ppm) (2.22 ppm) The final product was characterized by Mass Spec=(918.7169 observed; theoretical=918.7099) as well as $^1$H-NMR.

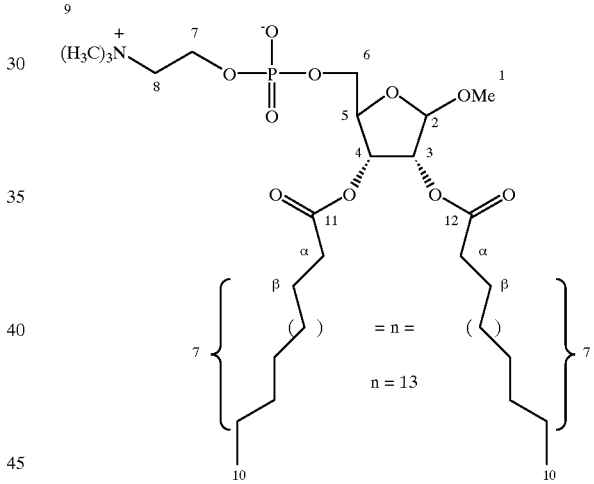

$^{13}$C-NMR Assignment for DARPC

EXAMPLE 2

Supramolecular Structures: 'Carbohydrosomes'

DLRPC, DMRPC and DARPC self-assemble into liposome-like structures in aqueous solution. To obtain these vesicles, DMRPC was deposited on a slide and water is added. After incubation at 40° C., myelin figures were observed growing from the solid lipid center as the lipid rehydrates. Vesicles, most likely multilamellar, were released from these myelin figures. Such structures are termed carbohydrosomes.

EXAMPLE 3

Thermal Analysis

The phase-transition temperatures ($T_m$) of the bilayers formed by DLRPC, DMRPC and DARPC were determined by modulated differential scanning calorimetry (MDSC).

DLRPC exhibited a $T_m$ of 15.75±0.05° C., 16° C. higher than the $T_m$ of the glycerol analog DLPC (−1.1±0.8° C.). A melting temperature of 29.6±0.3° C. was observed for DMRPC. This $T_m$ was approximately 6° C. higher than the phase-transition of DMPC (23.5° C.). The increase in $T_m$ for both DLRPC and DMRPC indicated a more stable state below the $T_m$. Interestingly, DARPC possessed a melting temperature of 63.5±0.6° C., which is slightly below the phase transition temperature of DAPC (66° C.). For DARPC, the similarity in $T_m$ was not entirely unexpected since tail—tail interactions contribute more to the $T_m$ as the tail length increases. Surprisingly, the phase transitions for the carbohydrate-based lipid systems were all broader than the phase transitions observed for the corresponding glycerol based lipids. At the phase-transition temperature, the bilayer transformed from the gel-liquid crystalline phase in glycerol based phospholipids such as DLPC and DMPC. This endothermic process was observed as two discreet events. A small pre-transition peak, corresponding to the conversion from a lamellar gel ($L_\beta$) phase to rippled gel ($P_\beta$) phase, occurred below a much larger sharp main transition peak corresponding to conversion of the $P_\beta$ phase to the liquid crystalline $L_\alpha$ phase. The temperature at which the pre-transition existed as well as the enthalpy of the transition both changed as a function of tail length in a linear pattern. This presence of two well-defined phase transitions was not observed for the carbohydrate-based lipids.

A linear relationship between the phase-transition temperature and the enthalpy exists for the glycerol-based phospholipids (FIG. 1). The literature values for the glycerol based phospholipids (solid squares), experimentally determined data for the glycerol-based phospholipids (open diamonds), and for the novel carbohydrate-based (checked squares) phospholipids were plotted as well. The enthalpy of DLRPC was 3.3±0.3 kcal/mol and was approximately double the enthalpy observed for DLPC (1.5 kcal/mol). The enthalpy of transition for DMRPC was 6.1±1.0 kcal/mol and was similar to the enthalpy for DMPC (measured 5.6±1.1 kcal/mol; literature 5.9±0.6 kcal/mol). (Marsh, D. *CRC Handbook of Lipid Bilayers*; CRC Press: Boca Raton, Fla., United States of America, 1990.) As the tail length increased from C12 to C14, the $T_m$'s and enthalpies of the carbohydrate-based lipids approached those of the glycerol-based lipids. This is consistent with tail—tail interactions becoming more important as tail length increases, reducing the influence of backbone modification on $T_m$. See FIG. 1.

The $T_m$'s of DAPC and DARPC were similar but the enthalpy of the carbohydrate-based DARPC was significantly lower than that of DAPC. The DAPC enthalpy was 12.6±0.7 kcal/mol (literature=11.93 kcal/mol) (Marsh, D. *CRC Handbook of Lipid Bilayers*; CRC Press: Boca Raton, Fla., United States of America, 1990.) while DARPC, the carbohydrate analog, possesses an enthalpy of 5.1±1.5 kcal/mol. This indicates that the carbohydrate backbone is likely destabilizing the bilayer membrane.

In nature, cell membranes contain a mixture of different phospholipids. The ability of phospholipids to mix with each other is easily investigated with MDSC. If two lipids mix without forming separate domains, then a single intermediate peak is observed between their respective phase-transition temperatures. If mixing is incomplete, two separate phase transition temperatures corresponding to the two fractions are observed. Although DMPC and DMRPC as well as DLPC and DLRPC possess chemically and structurally different backbones, (i.e., glycerol vs. carbohydrate), a single mixed bilayer is formed. For example, lipid mixtures with a single transition temperature between 29° C. (100% DMRPC) and 23.5° C. (100% DMPC) are formed by simply varying the DMPC/DMRPC ratios, illustrating that DMRPC mixes with DMPC to form mixed lipid bilayers.

Modulated Differential Scanning Calorimetry

Thermal Analysis of DLRPC 1–2 mgs of lipid were hermetically sealed with 9–11 mL water in an aluminum pan. The modulation was set to ±1.00° C. every 40 seconds and the pan was equilibrated at −15° C. The temperature was increased at 0.5° C./min to 70° C. where the temperature was held for 2 minutes. The temperature was then reduced to −10° C. and held at this temperature for 2 minutes. This heating-cooling cycle was repeated two more times before the sample was held isothermal at −10° C. for 20 minutes. Integrating under the heat flow peak curve of the main peak provides the enthalpy of the transition. TA Instruments Universal Analysis computer program (available from TA Instruments of New Castle, Del., United States of America) was used to analyze the data. DLRPC has a $T_m$ of 15.75° C. and an enthalpy of 3.3 kcal/mol.

Thermal Analysis of DMRPC

The same modulated differential scanning calorimetry method used on DLRPC was employed to obtain thermotropic data on DMRPC. DMRPC exhibited a $T_m$ of 29.6° C. and an enthapy of 6.1 kcal/mol.

Thermal Analysis of DARPC

The same modulated differential scanning calorimetry method used on DLRPC was employed to obtain thermotropic data on DARPC. DARPC exhibited a $T_m$ of 63.5° C. and an enthapy of 5.1 kcal/mol.

Thermal Analysis of DLRPA

The same modulated differential scanning calorimetry method used on DLRPC was employed to obtain thermotropic data on DLRPA. Instead of using water to hydrate the samples however, the following 5 buffers were utilized: a) 0.1 M KCl/HCl at pH 1.5, b) 0.1 M KCl/HCl at pH 4.14, c) 0.1 M Tris-HCl at pH 7.4, d) 0.01 M sodium borate at pH 8.44, and e) 0.01 M sodium borate at pH 9.5. The thermotropic behavior as a function of pH was obtained and is summarized in Table 1.

TABLE 1

Thermotropic Behavior of DLRPA as a function of pH

| pH | $T_m$(° C.) |
|---|---|
| 1.5 | 45 |
| 4.14 | 34 |
| 7.4 | 31 |
| 8.4 | 29 |
| 9.5 | 18 |

EXAMPLE 4

X-ray Diffraction Studies

Multilamellar suspensions of lipid were formed by hydrating 3–10 mgs of lipid in 1–2 mL water at a temperature above the phase-transition temperature of the lipid. This mixture was cycled below the phase-transition temperature 3 times with vortexing between each cycle. (McIntosh, T. J.; Simon, S. A.; MacDonald, R. C. *Biochim. Biophys. Acta* 1980, 597, 445–463.) The mixture was centrifuged to provide a hydrated pellet of multilamellar bilayers. Pellets of DMRPC/cholesterol mixtures do not easily form usable pellets for X-ray studies. The pellet was transferred to a sealed quartz-glass X-ray capillary which was mounted in a temperature controllable chamber on a point-focus collimator. A stationary anode Jerrel-Ash™ generator (Jerrel-Ash Div., Fisher Scientific Co., Waltham, Mass., United States of America) was used to produce copper Kα X-radiation. (McIntosh, T. J. *Biophys. J.* 1980, 29, 237–246.) Diffraction patterns were obtained using a flat plate film cassette loaded with KODAK™ DEF X-ray film. Specimen to film distances were ~10 cm with exposure times of 2–6 hours. The low angle reflections were in accordance with Bragg's law, $2d \sin\theta = h\lambda$ where $\lambda$ is the wavelength (1.54 Å), d is the repeat period, h is the number of the diffraction order and $\theta$ is the Bragg angle. Densiometry was performed with a commercially available JOYCE-LOEBL™ microdensiometer Model MK IIIC.

X-ray diffraction of DLRPC

For DLRPC at 10° C., patterns with wide-angle reflections at 7.7 Å, 6.1 Å, 4.9 Å, 4.6 Å, and 3.9 Å were observed. These X-ray data were consistent with hydrocarbon chains crystallized in the plane of the bilayer; this is commonly called an $L_c$ phase. (Blaurock, A. E.; McIntosh, T. J. Biochemsitry 1986, 25, 299–305.)

X-ray diffraction of DMRPC

For DMRPC at 22° C., X-ray patterns consisted of several sharp wide-angle reflections at 7.74 Å, 6.2 Å, 4.1 Å and 3.9 Å. These X-ray data were consistent with hydrocarbon chains crystallized in the plane of the bilayer; this is commonly called an Lc phase.

X-ray diffraction of DARPC

X-ray diffraction patterns of DARPC at 22° C. revealed the effect of longer-chains on bilayer packing. Wide-angle reflections were observed at 4.1 Å and 3.8 Å. These data indicated a gel phase similar to DAPC instead of an Lc phase seen in DLRPC and DMRPC. The bilayer formed by DARPC was more similar to the bilayers formed by glycerol-based phospholipids.

To further characterize the structures formed by DLRPC, DMRPC, and DARPC, X-ray diffraction data were obtained. DLRPC and DMRPC exhibited similar phases below and above the $T_m$. For DLRPC at 10° C., patterns with wide-angle reflections at 7.7 Å, 6.1 Å, 4.9 Å, 4.6 Å, and 3.9 Å were observed. For DMRPC at 22° C., X-ray patterns consisted of several sharp wide-angle reflections at 7.74 Å, 6.2 Å, 4.1 Å and 3.9 Å. These X-ray data were consistent with hydrocarbon chains crystallized in the plane of the bilayer; (Blaurock, A. E.; McIntosh, T. J. *Biochemistry* 1986, 25, 299–305.); this is commonly called an Lc phase. Such crystalline hydrocarbon chain packing is not typically observed with glycerol-based phospholipids below their phase-transition temperature. (Marsh, D. *CRC Handbook of Lipid Bilayers*; CRC Press: Boca Raton, Fla., United States of America, 1990.) This crystalline chain packing indicated a stable bilayer packing arrangement within the carbohydrosome below the phase-transition temperature. This conclusion is supported by the increased $T_m$ and enthalpy observed for DLRPC and DMRPC.

X-ray diffraction patterns of DARPC at 22° C. revealed the effect of longer-chains on bilayer packing. Wide-angle reflections are observed at 4.1 Å and 3.8 Å. These data indicated a gel phase like in DAPC instead of an $L_c$ phase seen in DLRPC and DMRPC. The bilayer formed by DARPC was similar to the bilayers formed by glycerol-based phospholipids. Since the phase transition was from a gel-liquid crystalline phase instead of a $L_c$-liquid crystalline phase, the enthalpy was expected to be lower, consistent with a gel-liquid crystalline phase transition. The enthalpy of transition for DARPC was approximately half that exhibited for the glycerol based DAPC (see FIG. 1). These data suggest that the carbohydrate backbone was likely destabilizing the gel state or afforded a decrease in cooperativity between the long-chain phospholipids in the bilayer.

EXAMPLE 5

Cholesterol Interactions

Cholesterol is present at varying concentrations in biological membranes and plays a role in modifying bilayer physical properties. The consequences of adding cholesterol to a bilayer was reviewed by McMullen et al. (McMullen, T. P. W.; et al. *Biochemistry* 1993, 32, 516–522.) and include the following: a broadening and eventual elimination of the cooperative gel-liquid crystal transition of the bilayer, a decrease/increase in the orientational order of the hydrocarbon chains below/above the phase transition, the expansion/condensation of the gel/liquid-crystalline bilayer, a decreased gel phase chain tilt angle, an increase/decrease in the passive permeability of the gel/liquid-crystalline phases, and loss of a pre-transition at low cholesterol concentrations. With the addition of cholesterol, both the pre and main phase transitions decrease. The pre-transition peak disappears when the cholesterol concentration is 5–10 mol %. Higher cholesterol concentrations are necessary to abolish completely the main transition. For example, the enthalpy of transition for saturated diacylglycerol-based phospholipids reaches zero regardless of chain length at about 50 mol % cholesterol. (McMullen, T. P. W.; et al. *Biochemistry* 1993, 32, 516–522.)

A similar trend was observed with the carbohydrate-based lipids of the present invention. The enthalpy was zero at 50 mol % cholesterol for DMRPC. For the glycerol-based phospholipid, cholesterol packed in the bilayer membrane with its hydroxyl group at the same level as the acyl groups. In this structural arrangement, cholesterol primarily interacted with the tails and not the head group or backbone. Consequently, substitution of the glycerol by ribose did not dramatically alter placement of cholesterol within the bilayer.

Phospholipids possessing tails of 17 carbons or less have phase-transition temperatures that increase as cholesterol content increases. (McMullen, T. P. W.; et al. *Biochemistry* 1993, 32, 516–522.) The temperature increase is a function of cholesterol concentration and affords up to a 17° C. increase in temperature at 40 mol % cholesterol for DMPC. A different effect of cholesterol on bilayer structure is observed with long chain glycerol derivatives. As the chain length increases to greater than 17, the phase-transition temperature decreases. A mismatch between the hydrophobic length of the cholesterol molecule and the length of the hydrophobic core of the lipid molecule determines if an increase or decrease in $T_m$ is observed. (McMullen, T. P. W.; et al. *Biochemistry* 1993, 32, 516–522.) Thus, cholesterol can stabilize or destabilize a gel state.

For DMRPC, a slight decrease in phase-transition temperature was observed. The phase-transition temperature decreased from ~30° C. at 0 mol % cholesterol to ~27° C. at 35 mol % cholesterol. This result is unexpected since the tail length is less than 17 carbons. The carbohydrate backbone of DMRPC likely altered the effective hydrophobic length of the bilayer area (this DMRPC is similar to longer tail systems). There was a slight destabilization of the bilayer membrane with the incorporation of cholesterol as indicated by the decrease in phase-transition temperature. This suggests a mismatch between the hydrophobic length of DMRPC and cholesterol disrupting the interactions between DMRPC in the bilayer. X-ray data on 20 mol % cholesterol/DMRPC confirmed the $L_c$ state. A repeat period of 54 Å was observed with weak reflections at crystal spacings of 3.7 and 4.8 Å.

EXAMPLE 6

Phospholipase Assays on DMRPC

The pH-stat phospholipase assays were performed on a Metrohm 718 STAT Titrino pH-stat following a procedure described by Yuan et al. (Yuan, W.; Berman, R. J.; Gelb, M. H. *J. Am. Chem. Soc.* 1987, 109, 8071–8081; Deems, R. A.; Dennis, E. A. *Methods Enzym* 1981, 71, 703–710.) Before the assays were performed, the pH-stat was calibrated at pH 7 and pH 4. The NaOH (0.01 N) titrant was standardized by titration to pH 8.65 with a weighed amount of potassium hydrogen-phthalate in 40 mL of Dl water. The lipid was transferred to a 5 mL round bottom flask in methylene chloride/methanol (98/2) and the solvent was removed by rotoevaporation. High vacuum then removed trace amounts of remaining solvent. The lipid film was rehydrated with 2 mL of an aqueous solution containing TRITON X-100™ detergent (Sigma Chemical Company, St. Louis, Mo.) (40 mM) and $CaCl_2$ (10 mM) and then sonicated briefly to solubilize the lipids.

Next, the solution was immersed in a temperature-controlled bath at 40° C. and stirred with a magnetic stir bar. A stream of argon was passed over the reaction mixture to prevent $CO_2$ absorption. A microelectrode (Metrohm 6.0224.100 pH 1–11/0–60° C. Idrolyte) was inserted through the top of the reaction vessel along with the dosing tube from the pH-stat. The reaction mixture was adjusted to a pH of 8.2 by addition of NaOH. Next, 0.2 units of $PLA_2$ (naja naja venom, Sigma Chemical Company, St. Louis, Mo.) (0.1 units/mL) was added to the reaction and the reaction started. The pH was allowed to drop to 8.0 and held at this value by addition of NaOH. At pH 8, the fatty acids were almost completely ionized; therefore, the amount of base added as a function of time indicates cleavage of the ester bond.

Enzymes play an important role in phospholipid function and metabolism. (Hanahan, D. J. *A Guide to Phospholipid Chemistry*, Oxford University Press: New York, 1997; Cao, Y.; Tam, S. W.; Arthur, G.; Chem, H.; Choy, P. C. *J. Biol. Chem.* 1987, 262, 16927–16935.) In the biological milieu, phospholipase $A_2$ ($PLA_2$) catalyzes the hydrolysis of the fatty acid from the sn-2 position of the glycerol backbone yielding a free fatty acid and a lyso-phospholipid. Glycerol based phospholipids such as DMPC and DPPC are known $PLA_2$ substrates. Synthetic lipids such as the cyclopentanoid-based phospholipids have been tested as substrates of $PLA_2$. (Lister, M. D.; Hancock, A. J. *J. Lipid Research* 1988, 29, 1297–1308.) While a few cyclopentanoid analogs were not found to be substrates for $PLA_2$, the majority of the lipids were hydrolyzed as they maintain the basic glycerol backbone.

In this Example, enzymatic activity was recorded using a pH-stat, which maintains a specific pH by adding base during the enzymatic reaction. During these assays, DMPC was hydrolyzed with an initial average rate of 6.19 E-08 (moles NaOH/minute) (std dev 6.72E-10). However, DMRPC is not hydrolyzed.

Next, whether DMRPC inhibits $PLA_2$ activity was investigated. Using DMPC (5 mM) as a substrate, DMRPC was added to the reaction mixture at varying concentrations. DMRPC (6.32E-08 (std. dev. 1.36E-08)) did not exhibit a significant deviation from the DMPC standard (6.19 E-08 (std. dev. 6.72E-10)). Additional studies using varying concentrations of DMRPC confirmed that adding as much as 4 mM DMRPC to the assay mixture did not yield a significant hydrolysis rate decrease. These data indicate that DMRPC is likely neither a $PLA_2$ inhibitor or substrate. With a change in structure, different carbohydrate-based phospholipids could inhibit $PLA_2$.

EXAMPLE 7

DMRPC Leakage Studies Utilizing DMRPC

The following procedure is adapted from Weinstein et al. (Weinstein, et al., *Self-Quenching of Carboxyfluorescein Fluorescence: Uses in Studying Liposome Stability and Liposome-Cell Interaction*; Weinstein, J. N.; et al., Ed.; CRC Press, Inc.: Boca Raton, Fla., United States of Amenica 1984; Vol. 3, pp 183–204.) and was successfully used in DMPC control experiments. Immediately before use, the carbohydrate-based lipid DMRPC, was passed through a C-18 SEP PAK™ column using a solvent system of 10% $MeOH/CH_3CN$. Both the cholesterol and DMRPC were dissolved in chloroform and mixed. The mixtures were dried by rotoevaporation in a 100 mL round bottom flask before being thoroughly dried by high vacuum. Multilamellar vesicles were formed by adding 50 mM carboxyfluorescein (CF) solution in 20 mM PBS buffer and agitating the mixture with a stir bar at 50° C. for 20 minutes. The resultant cloudy solution was then extruded 5 times under pressure at 50° C. through two 200 nm PORETICS® polycarbonate filters (available from Poretics Corporation of Livermore, Calif., United States of America) using a commercial extruder (available under the trademark LIPEX™ from Northern Lipids, Inc. of Vancouver, British Columbia, Canada). This procedure yielded a homogenous solution that was annealed by cycling above 50° C. three times. The size of the liposomes was determined using dynamic light scattering. In order to remove unencapsulated CF, the sample was next filtered through a SEPHADEX™ G-50 column at 2200 rpm for 10 minutes. The filtered liposomes were diluted into osmotically equivalent 20 mM PBS buffer at pH 7.4 and the fluorescence intensity was measured over time. To obtain 100% release of the dye, the vesicles were incubated with 20 μl of 10% TRITON X-100™ detergent for 5 minutes at 50° C.

Mixtures of phospholipids containing cholesterol are often studied since cholesterol provides increased mechanical stability. (Needham, D.; Nunn, R. S. *Biophys. J.* 1990, 58, 997–1009; Juliano, R. L. *Pharmacokinetics of liposome-encapsulated drugs*; Juliano, R. L., Ed.;Elsevier/North-Holland Biomedical Press: New York, 1981, pp 391–407.) Leakage assays with 0%, 30%, and 50% cholesterol/DMRPC were conducted with ~260 nm carbohydrosomes. Although vesicles of 100% DMRPC were formed and observed with particle sizing experiments, the vesicles were too fragile to survive the SEPHADEX™ G-50 column separation procedure that was used to remove remaining unencapsulated carboxyfluorescein from the vesicle suspension.

Negligible release of carboxyfluorescein is observed in the first 20 minutes for both 70/30 DMRPC/cholesterol (258.0 nm+/−113.5 nm) and 50/50 DMRPC/cholesterol (276.1 nm +/−118.6) vesicles. These data indicate that carbohydrosomes are able to encapsulate carboxyfluorescein and retain the encapsulated dye over the first 20 minutes as compared to DMPC vesicles that release dye over the first 20 minutes. The slight negative slope of this line is due to bleaching of the carboxyfluorescein. Compared to DMPC however, lower numbers of carbohydrosomes survive the column as indicated by the smaller fluorescence increase after lysing with TRITON X-100™ detergent.

Although the 70/30 DMRPC/cholesterol carbohydrosomes capture carboxyfluorescein, release occurs relatively rapidly, completing after 16 hours at 22° C. Unlike the 70/30 DMRPC/cholesterol carbohydrosomes however, the 50/50 DMRPC/cholesterol vesicles were able to maintain and to release carboxyfluorescein over a time frame of approximately 24 days at 22° C.

As discussed herein above, one of the most wide-spread uses of liposomes is as drug delivery vehicles in warm-blooded vertebrates, including humans. Drugs such as the anti-cancer agent doxorubicin are loaded into liposomes that provide both evasion from the immune system as well as improved pharmacokinetics. Two approaches exist on drug release from liposomes. In one, triggered release by factors such as heat or pH is desired, while in the other, a sustained drug release over time is sought. In this Example, release of the self-quenching dye 5(6)-carboxyfluorescein (encapsulated in 5 mg/mL) was monitored over time by preparing carboxyfluorescein-containing carbohydrosomes using the high-pressure extrusion method. Mixtures of phospholipids containing cholesterol were studied since cholesterol provides increased mechanical stability. (Needham, D.; Nunn, R. S. Biophys. J. 1990, 58, 997–1009; Juliano, R. L. *Pharmacokinetics of liposome-encapsulated drugs*; Juliano, R. L., Ed.; Elsevier/North-Holland Biomedical Press: New York, 1981, pp 391–407.) Leakage assays with 0%, 30%, and 50% cholesterol/DMRPC were conducted with ~260 nm carbohydrosomes.

Release of carboxyfluorescein is observed in the first 20 minutes for both 70/30 DMRPC/cholesterol (258.0 nm +/−113.5 nm) and 50/50 DMRPC/cholesterol (276.1 nm +/−118.6) composition. These data indicate that carbohydrosomes are able to encapsulate carboxyfluorescein and maintain the dye over the first 20 minutes. Although the 70/30 DMRPC/cholesterol carbohydrosomes capture carboxyfluorescein, release occurs relatively rapidly, completing after 16 hours at 22° C. Unlike the 70/30 DMRPC/cholesterol carbohydrosomes, however, the 50/50 DMRPC/cholesterol vesicles were able to maintain and release carboxyfluorescein over a time frame of greater than 24 days at 22° C.

EXAMPLE 8

Synthesis and Characterization of a Dianionic Carbohydrate-Based Phospholipid

The synthesis and thermotropic properties of bis-(2,3-lauroyl)-1-methoxy-5-ribo-phosphatidic acid (DLRPA), an anionic carbohydrate-based analog of dilauroyl phosphatidic acid (DLPA), is disclosed in this Example.

Phosphorous oxychloride was used successfully to synthesize the subject compound. $POCl_3$ was dissolved in dry $CH_2Cl_2$ before adding an excess of TEA. Compound 4 was dissolved in dry $CH_2Cl_2$ and added drop wise to the cooled (0° C.) reaction mixture. After stirring at room temperature, water was added to form the desired final product. The product was isolated by a series of precipitations before being purified by C18 SEP PAK™ column chromatography (10% $MeOH/CH_2Cl_2$) to yield 18 in a 31% yield.

bis-(2,3-lauroyl)-1-methoxy-5-(phospho)-ribose, 18

$POCl_3$ (1.0 g, 6.52 mmol) was added to 250 mL of dry $CH_2Cl_2$ under $N_2$ before adding TEA (5.5 mL, 41.6 mmol). This mixture was cooled to 0° C. before slowly adding thoroughly dried 4 (0.05 g, 0.10 mmol) dissolved in 50 mL dry $CH_2Cl_2$. After addition, the reaction mixture was stirred under $N_2$ for 10 minutes before it was removed from the ice bath. The reaction mixture was stirred at 22° C. for an additional 5 minutes before adding 10 mL $H_2O$ and then stirring for 10 minutes. Solvent was removed by rotoevaporation and the remaining water was removed by high vacuum overnight. The product was extracted by washing with diethyl ether. After removing the ether by rotoevaporation, the final product 18 (0.02 g, 0.03 mmol) was precipitated from MeOH in 31% yield.

The final product was desalted using a C18 SEP PAK™ column (10% $MeOH/CH_2Cl_2$) before use. $^1$H-NMR ($CD_3CN$, 400 MHz, ppm): H(4), 5.172 (1H, t, J=16 Hz); H(3), 5.126 (1H, d, J=2.4 Hz); H(2), 4.855 (1H, s); H(5), 4.196 (1H, m); H(6), 3.938 (1H, m); H(6), 3.846 (1H, m); H(1), 3.337 (3H, s); H(b), 1.539 (4H, m); H(—CH2)n—), 1.261 (m); H(ω), 0.868 (t, J=7.2 Hz). $^{13}$C-NMR($CD_3CN$, 400 MHz, ppm): C(7), 177.497; H(8), 173.290; C(2), 107.090; C(5), 81.015; C(3), 75.132; C(4), 72.439; C(6), 66.502; C(1), 55.570; C(—($CH_2$)$_n$—), 32.674, 30.402, 01.1.2, 29.795, 25.645, 25.531, 23.411; C(ω), 14.402. ($^{31}$P-NMR=1.54 ppm) High Resolution FAB Mass Spectrometry ((MH)+theoretical=608.3707/observed=608.3662).

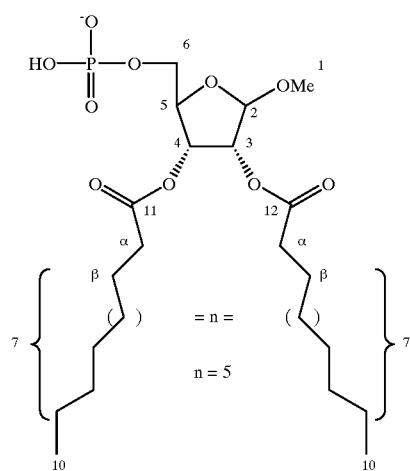

$^{13}$C-NMR Assignment for DLRPA

EXAMPLE 9

Thermal Analysis of DLRPA

The effect of pH on the phase-transition temperature of DLRPA supramolecular structures was probed using modulated differential scanning calorimetry. Experiments were performed in the following 5 solutions: a) 0.1 M KCl/HCl at pH 1.5, b) 0.1 M KCl/HCl at pH 4.14, c) 0.1 M Tris-HCl at pH 7.4, d) 0.01 M sodium borate at pH 8.44, and e) 0.01 M sodium borate at pH 9.5. The $T_m$ of DLRPA was observed to decrease in a step-wise manner from ~45° C. at pH 1.5 until ~18° C. at pH 9.5.

While the physical state of the dianionic head group changes with pH, the tail groups are still the main contributor to the phase-transition temperature. For short chain phosphatidic acids such as dilauroyl phosphatidic acid, the $T_m$ decreases as the pH increases since the electrostatic interactions between adjacent head groups destabilize the packing. A similar pH dependent profile exists for DLRPA as compared to DLPA. (Van Dijck, P. W. M.; et al., *Biochim. Biophys. Acta.* 1978, 512, 84–96.) Both exhibit a decrease in $T_m$ with an increase in pH. This profile reflects the increase in charge with loss of successive protons from the phosphate.

Increased electrostatic repulsion between lipid molecules yields a decreased gel state stability and therefore, a decrease in phase-transition temperature. Both DLPA and DLRPA lose the first proton at ~pH 3–4. DLRPA loses the second proton at pH ~8.5 compared to pH ~7 for DLPA. The increase in phase-transition temperature for DLRPA at higher pH indicates higher gel-phase stability and is likely a consequence of increased backbone—backbone interactions. A similar conclusion was reached for the zwitterionic carbohydrate-based phospholipids disclosed herein above. Dilauroyl ribo-phosphatidylcholine (DLRPC) and dimyristoyl ribo-phosphatidylcholine (DMRPC), both exhibited higher phase-transition temperatures and enthalpy than their glycerol analogs.

The synthesis and characterization of a novel carbohydrate-based phospholipid (DLRPA) containing a phosphatidic acid head group is thus presented in Examples 8 and 9. The thermotropic properties of this novel molecule at different pH's mirror those of conventional glycerol based phospholipids (DLPA). The increase in pKa between DLRPA and DLPA corroborates with known data on zwitterionic carbohydrate-based phospholipids, which indicates more stable packing in the bilayer due to ribose backbone—backbone interactions.

EXAMPLE 10

Synthesis of the Carbohydrate-based Dicationic Lipid

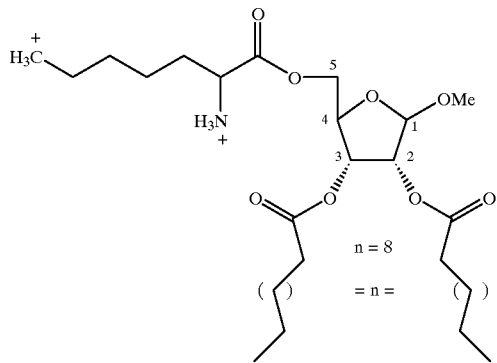

Structure of 1-methoxy-2,3-dilauroyl-ribo-5-lysine (DLR-Lys)(n=8)

Currently, research has focused on optimizing the transfection efficiency of lipid-based transfection agents by modifying the cationic head group, the hydrophobic lipid group and the linker between the two. Banerjee et al. have recently synthesized non-glycerol-based surfactants and tested their utility as transfection agents; the non-toxic compounds exhibited high transfection efficiency in vitro. Jacobson, K.; Papahadjopulos, D. *Biochemistry* 1975, 14, 152–161. In this Example, a novel cationic lipid containing ribose as the backbone and linker was synthesized and characterized.

Two C12 chains were attached at the 2- and 3-positions of the ring through ester linkages. At the 5-position, a dicationic residue based upon lysine was attached with an ester linkage, affording a dicationic lipid. The 1-position was protected with a methoxy protecting group. The systematic name for this compound is 1-methoxy-2,3-dilauroyl-ribo-5-lysine, abbreviated as DLR-Lys.

This novel carbohydrate-based lipid has potential advantages over other cationic lipids utilized for transfection. First, it is based upon the biodegradable ribose unit. Second, the 1-position of the ribose ring permits easy derivitization. Different groups (including targeting moieties, additional cationic groups to increase DNA-lipid interactions, poly (ethylene-glycol) to impart stealth character, and labels for transfection mechanism studies) can all be attached at this position. Third, the synthesis of this molecule is easily amenable to a combinatorial approach. Indeed, it is facile to vary the tail lengths, head group and moieties attached to the 1 position in a systematic way.

Methyl-2,3-di-O-lauroyl-β-D-ribo-5-lysine, 20 (DLR-Lys), was synthesized as shown in Scheme 2. The first step involved protecting the primary hydroxide of 1 using trityl chloride. Purification of 2 was accomplished by silica gel column chromatography in 87% yield with an eluent of 3% methanol/chloroform. Next, a DCC coupling with DMAP and lauric acid in DMF afforded compound 3. The compound was purified on a silica gel column with the eluent of 9/1 hexane/ethyl acetate, then immediately dissolved in aqueous acetic acid to remove the trityl protecting group. Compound 4 was subsequently purified by silica gel column chromatography (eluent 7/3 hexane/ethyl acetate) with an overall yield of 88% from 2 to 4. A DCC coupling was used to couple the free acid of CBZ-protected lysine to the alcohol at the 5-position of the ribose ring forming 19 in a 70% yield. The CBZ protecting groups were removed by standard catalytic hydrogenation using a Pd catalyst to afford the final product DLR-Lys 20. The product was purified through alumina column chromatography (65/25 $CHCl_3/CH_3OH$ to 65/25/4 $CHCl_3/CH_3OH/H_2O$) followed by a C18 SEP PACK™ column (load with 10/90 MeOH/ACN, elute with 100% $CHCl_3$) to yield DLR-Lys in a 38.9% yield.

Scheme 2 - Synthesis of DLR-Lys

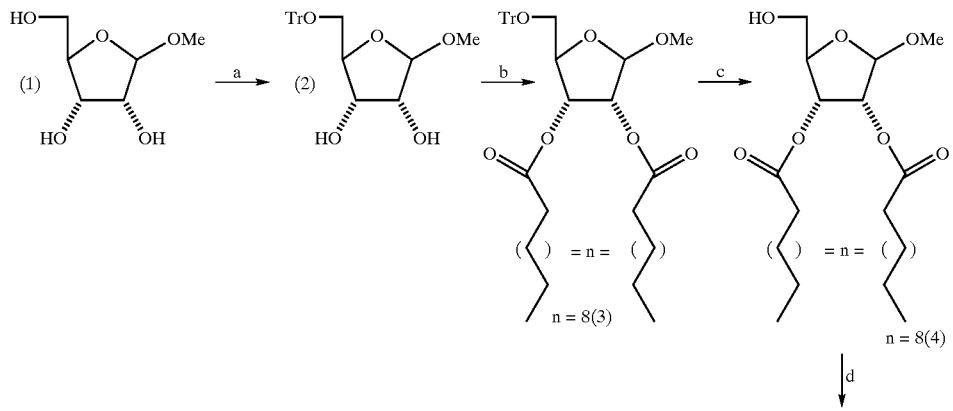

-continued

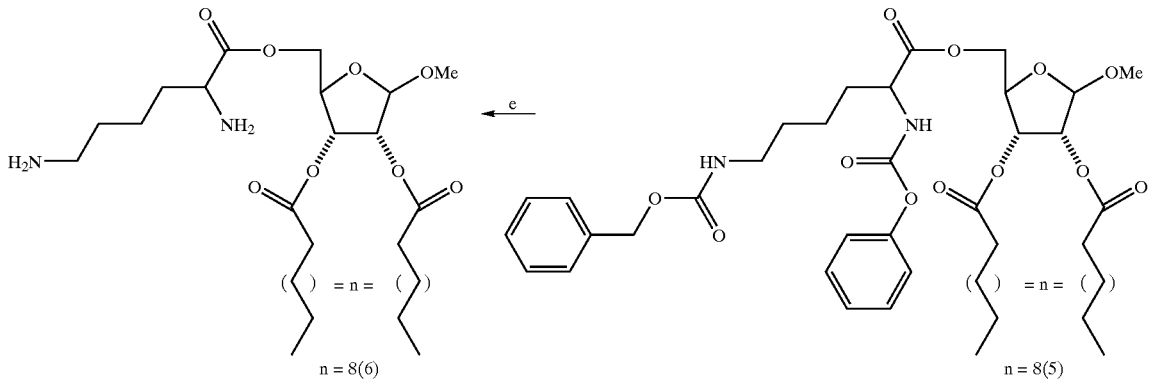

a) TrCl, C₅H₅N, 3 hrs., 120° C., b) DCC, DMAP, lauric/myristic/arachadonic acid, DMF, 48 hrs., 60° C., c) acetic acid, H₂O, 12 hrs., 50° C., d)N, N'-di-carbobenzyloxyl-L-lysine, DPTS, DCC, CH₂Cl₂, 20 hrs., 22° C., e) 10% Pd/C, H₂, 40 PSI, 50/50 acetic acid/MeOH, 1 Hr, 22° C.

bis-(2,3-lauroyl)-1-methoxy-5-(CBZ-lysine)-ribose, 19

CBZ lysine (0.60 g, 1.44 mmol), 4-dimethylamino-pyridinium-p-toluenesulfate (DPTS) (0.30 g, 1.01 mmol), and dicyclohexylcarbodiimide (DCC) (0.32 g, 1.53 mmol) were added to 4 (0.50 g, 0.94 mmol) in 120 mL of dry dichloromethane. After stirring under nitrogen at room temperature for twenty hours, 3.0 mL of 10% citric acid was added and stirred for twenty minutes. A white precipitate was filtered from the solution using a Buchner funnel; the precipitate was washed with cold tetrahydrofuran. The resultant solution was washed with 0.5N HCl, 5% NaHCO₃ and water before being dried with sodium sulfate. The product was filtered and the solvent evaporated using a rotoevaporator. Purification by silica column chromatography (20% ethyl acetate in hexane) produced 19 (0.61 g, 0.66 mmol) in a 69.8% yield.

bis-(2,3-lauroyl)-1-methoxy-5-(lysine)-ribose, 20

To remove the CBZ protecting group, 19 (0.03 g, 0.66 mmol) was dissolved in a 50/50 acetic acid/methanol solution. After adding 10% palladium on carbon, the solution was hydrogenated at 40 PSI for one hour. Filtration through celite removed the catalyst and the celite was washed with methanol. The acetic acid and methanol were removed by high vacuum. The product was dried and azeotroped three times with benzene to remove excess acetic acid. Acetonitrile/MeOH (9/1) was added to the flask and the precipitate filtered out. The remaining solution was fully evaporated before adding MeOH and the resultant precipitate was again filtered. This filtrate was concentrated and purified by alumina column chromatography (65/25 CHCl₃/CH₃OH to 65/25/4 CHCl₃/CH₃OH/H₂O) followed by a C18 SEP PACK™ (load with 10/90 MeOH/ACN, elute with 100% CHCl₃), producing 20 (0.17 g, 0.26 mmol) in a 38.9% yield. High Resolution FAB Mass Spectrometry ((MH)+ theoretical=657.5059/observed=657.5056) confirmed the product. A clean NMR was not obtained because of product instability.

EXAMPLE 11

Synthesis and Characterization of Derivatizable Carbohydrate-based Phospholipid

One advantage of using ribose as a phospholipid backbone is the open 1-position, which is available for attaching various moieties such as polyethylene glycol (PEG), biotin or 5(6)-carboxyfluorescein. Modifying the phospholipid off of the backbone provides 1) the ability to attach two similar or different moieties to the phospholipid molecule; 2) an opportunity to study the effect of derivatization at a non-head group site; and 3) the ability to attach moieties without disrupting the head group interactions in a bilayer.

In this Example, the synthesis of compound 30 was accomplished, as evidenced by high resolution mass spectrometry (see Scheme 3 and Scheme 4).

Scheme 3 - Synthesis of α/β α/β-D-ribofuranose 1-(N-carbobenzyloxy ethanolamine)-2,3-myristoyl-5-hydroxide

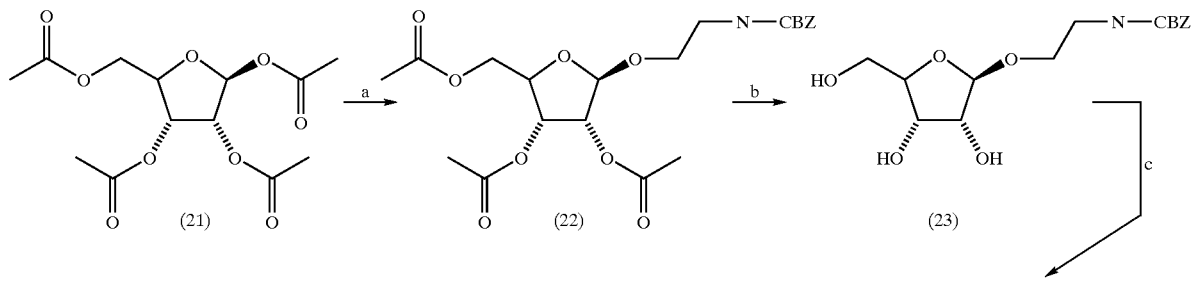

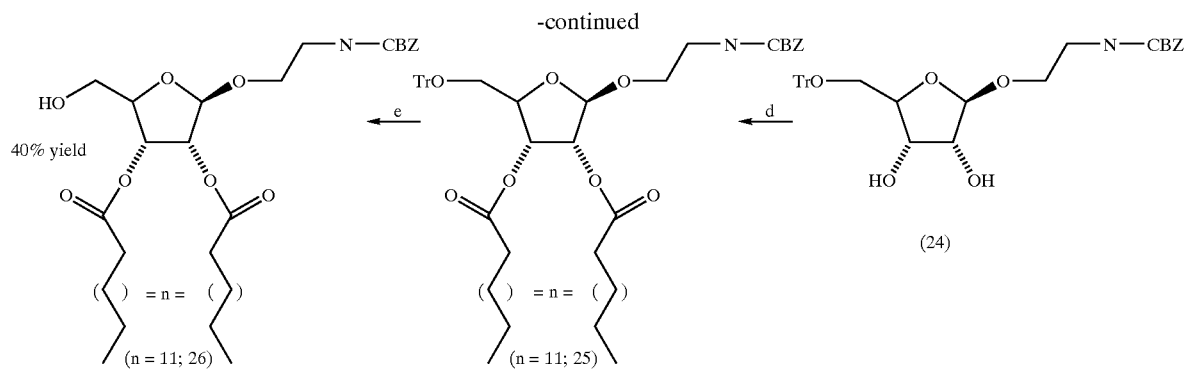

a) CBZ-Ethanolamine, SnCl₄, CH₃CN, 18 hrs., 80° C., b) NaOMe(cat), MeOH, 1 hr., 22° C., c) Trityl Chloride, DMAP, Pyridine, 3 hrs., 120° C., d) DCC, DMAP, Myristic Acid, CH₂Cl₂, 12 hrs., 50° C., e) Acetic Acid, H₂O, 12 hrs., 50° C.

Scheme 4 - Synthesis of α/β α/β-D-ribofuranose 1-ethanolamine-2,3-myristoyl-5-phosphocholine

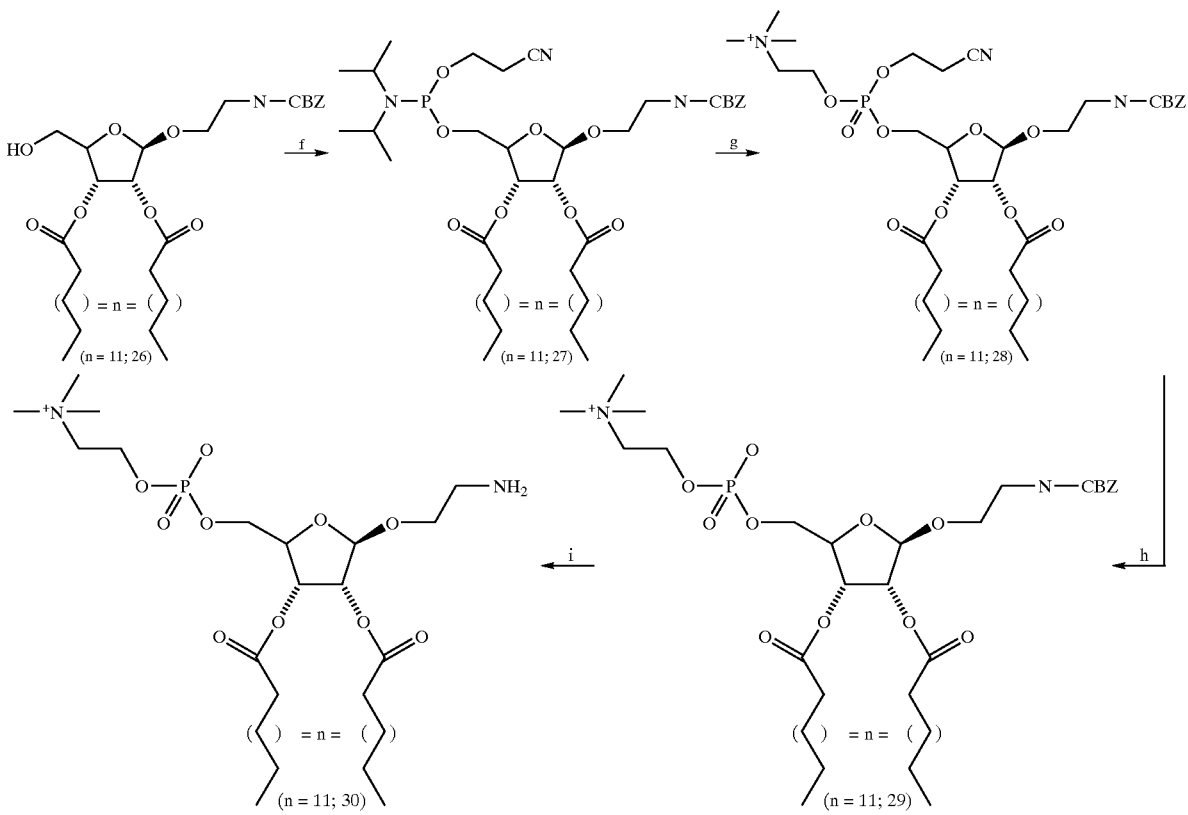

f) 2-cyanoethyl disopropyl-chlorophosphoramidte, DIPEA, CH₂Cl₂, 2 hrs., 22° C., g) tetrazole, choline chloride, I₂, ACN, 3 hrs., 22° C., h) TFA (aq), 3 hrs., 22° C., i) hn, 254nm, THF/MeOH, 3 hrs., 30° C.

As shown in Scheme 3, β-D-ribofuranose 1,2,3,5-tetraacetate 21 was reacted with benzyl N-(2-hydroxyethyl)-carbamate in the presence of SnCl₄ in dry acetonitrile for 18 hours. This mixture is washed with 1 M KF and water before being dried with Na₂SO₄ and purified by column chromatography (70/30 petroleum ether/ethyl acetate), yielding 22 in a 34% yield. 22 is actually a mixture of both the α and β anomers; however, there was a larger percentage of the β present (~1/9) because the SnCl₄ reaction favored the β addition. This mixture was carried throughout the remaining synthetic steps. The acetate protecting groups are removed by catalytic NaOMe in dry MeOH. 23 was purified by column chromatography (100% CHCl₃-5/95 MeOH/CHCl₃), providing 23 in a 72% yield. A trityl group is utilized to protect the 5 position of the ribose ring; 23 was reacted with trityl chloride in the presence of pyridine at 120° C. to yield 24. Column chromatography was again utilized to purify 24 (100% CH₂Cl₂-3/97 MeOH/CH₂Cl₂), which was obtained in a 79% yield.

To synthesize 26, standard DCC coupling conditions were used to attach the C14 chains to the derivatized ribose backbone. 24 was reacted with myristic acid, DMAP and DCC in dry CH$_2$Cl$_2$ at 50° C. for 12 hours. 25 was purified by column chromatography (9/1-hexane/ethyl acetate) before the trityl protecting group was removed by dissolving in aqueous acetic acid and heating at 50° C. overnight. After removing the acetic acid with column chromatography (8/2 hexane/ethyl acetate-7/3 hexane/ethyl acetate), 26 was isolated in 40% yield. The synthesis of compound 27 was accomplished by first reacting 26 with 2-cyanoethyl diisopropylchlorophosphoramidite followed by addition of choline chloride in the presence of tetrazole. The phosphorous (III) compound was subsequently oxidized to phosphorous (V) by I$_2$. Finally, the cyanoethyl protecting group of 28 was removed by dissolving the mixture in 0.14 M (aq) TEA and stirring for 3 hours at room temperature.

Compound 29 was isolated after extracting into MeOH, drying and extracting into CH$_2$Cl$_2$, and finally utilizing a neutral alumina column (100% CH$_2$Cl$_2$-25/75 MeOH/CH$_2$Cl$_2$) to provide product in a 70% yield. The product was confirmed by high-resolution mass spectrometry. To remove the CBZ protecting group from the primary amine at the 1-position of the ribose ring, irradiation at 254 nm in a quartz tube in THF/MeOH was used to provide product 30, which was characterized by mass spectrometry. The free amine of 30 can easily be reacted with the activated ester of moieties such as polyethylene glycol and carboxyfluorescein to form a derivatized carbohydrate-based phospholipid.

β-D-ribofuranose 1-(N-carbobenzyloxy ethanolamine)-2,3,5-triacetate, 22

β-D-ribofuranose 1,2,3,5-tetraacetate 21 (5.01 g, 15.73 mmol) and benzyl N(2-hydroxyethyl)-carbamate (7.67 g, 39.33 mmol) were azeotroped 3 times with dry acetonitrile under high vacuum at 50° C. Molecular sieves (4 Å, 4–8 mesh) were dried overnight at 140° C. under high vacuum. The dried molecular sieves were stirred with the above reagents for ½ hour in 250 mL dry acetonitrile before adding drop wise SnCl$_4$ (2.215 mL, 18.88 mmol) The reaction mixture was refluxed under nitrogen at 80° C. for 18 hours. After filtering though celite, all solvent was removed under high vacuum. The resultant oil was dissolved in ethyl acetate before washing with 1 M KF and water.

After drying and removing solvent by rotoevaporation, the product was purified by silica column chromatography (70/30 Petroleum ether/ethyl acetate) to yield compound 25 (2.54 g, 5.41 mmol) in a 34.4% yield. Thin layer chromatograpy (TLC) was utilized to follow the progress of the reaction (Rf=0.5 (1/1 petroleum ether/ethyl acetate)). $^1$H-NMR (CDCl$_3$) confirmed the presence of the CBZ protecting group; however, 22 was never purified sufficiently and therefore, the NMR was complicated. Peaks were observed from 7–7.4 ppm for the CBZ-protecting group, between 3–6 ppm for the sugar regions, and at ~2 ppm for the acetate protection group.

β-D-ribofuranose 1-(N-carbobenzyloxy ethanolamine)-2,3,5-hydroxide, 23

22 (2.54 g, 5.41 mmol) was dissolved in dry MeOH. Na (0.021 g, 0.54 mmol) was added to the reaction mixture and stirred for 20 minutes. The reaction was neutralized with weakly acidic resin. Purification was achieved with silica gel column chromatography (100% 39 CHCl$_3$-5/95 MeOH/CHCl$_3$) to yield 23 (1.28 g, 3.90 mmol) in a 72.4% yield. The product was characterized by TLC (Rf=0.17 (1/9 MeOH/CHCl$_3$) and FAB MS(MH+=328.14). Acetate protecting group removal was confirmed by the absence peaks at ~2 ppm by $^1$H-NMR (CDCl$_3$) experiments.

β-D-ribofuranose 1-(N-carbobenzyloxy ethanolamine)-2,3,-hydroxide-5-trityl, 24

23 (0.29 g, 0.89 mmol), DMAP (0.01 g, 0.09 mmol), and trityl chloride (0.29 g, 1.02 mmol) were dissolved in dry pyridine (40 mL) and stirred at 120° C. for 4 hours. Solvent was removed under high vacuum at 50° C. The residue was dissolved in CH$_2$Cl$_2$ and washed with water, 0.5 N HCl and again with water before being dried with Na2SO4. Silica gel column chromatography (100% CH$_2$Cl$_2$-3/97 MeOH/CH2Cl2) was utilized to purify 27 (0.40 g, 0.70 mmol) in a 79% yield. The product was characterized by TLC (Rf=0.3 (5/95 MeOH/CHCl$_3$) and FAB MS(MH+=570.2). In addition, 1H-NMR (CDCl$_3$) was also used for characterization. Peaks were observed at ~7.2 (m), 5.00 (s), 4.99 (s), 4.14 (t), 4.08 (m), 3.98 (d), 3.65 (m), 3.48 (m), 3.27 (m), and 3.19 (m) ppm. These peaks were consistent with those observed for the previous compounds.

β-D-ribofuranose 1-(N-carbobenzyloxy ethanolamine)-2,3-myristoyl-5-hydroxide, 26

25 (0.40 g, 0.70 mmol) and myristic acid (0.56 g, 2.46 mmol) were azeotroped 3 times in pyridine before dissolving in dry CH$_2$Cl$_2$ (200 mL), adding DCC (0.507 g, 2.457 mmol) and stirring at 50° C. for 12 hours. 10% Citric acid was added and stirred for 10 minutes to convert DCC to DCU before filtering the white precipitate (DCU) and washing with cold THF. This solution was rotoevaporated to ~100 mL before washing with 10% citric acid, 5% NaH$_2$CO$_3$, and water. The CH$_2$Cl$_2$ solution was dried with Na$_2$SO$_4$ before running a silica gel column (9/1 Hex/EtAc) to yield 25. The trityl protection group was immediately removed by dissolving 25 in acetic acid (aq) (150 mL) and stirring for 12 hours at 50° C. Purification was achieved by silica gel column chromatography (8/2 Hex/EtAc-7/3 Hex/EtAc) yielding 26 (0.208 g, 0.278 mmol) in 39% yield. The product was confirmed by Mass Spectrometry (MH+=749.9). TLC (Rf=0.27 (7/3 hexane/ethyl acetate) and $^1$H-NMR (CDCl$_3$) were also utilized for characterization. Peaks were observed at 7.3 (CBZ protecting group) ppm, 5.53 ppm, 5.37 ppm, 5.23 ppm, 5.09 ppm, 4.14 ppm, 3.78 ppm, 3.64 ppm, 3.38 ppm, 2.29 ppm, 1.55 ppm (tail), 1.24 ppm (tail), and 0.86 ppm (tail). These peaks were very broad perhaps due to supramolecular structures that form in solution.

β-D-ribofuranose 1-(N-carbobenzyloxy ethanolamine)-2,3-myristoyl-5-phosphocholine, 29

26 (3.18 g, 4.24 mmol) was azeotroped 3 times with acetonitrile before dissolving in dry CH$_2$Cl$_2$ (200 mL). N,N-diisopropyl ethylamine (1.48 mL, 8.48 mmol) was added before adding dropwise 2-cyanoethyl diisopropylchlorophosphoramidite (1.23 mL, 5.51 mmol) at 0° C. and stirring for 3 hours. The reaction was quenched with MeOH before rotoevaporating to dryness and removing residual solvent by high vacuum. After dissolving in CH$_2$Cl$_2$ the reaction mixture was washed with 5% NaH$_2$CO$_3$ and water before being dried over Na$_2$SO$_4$. Choline chloride (1.37 g, 33.30 mmol) was added to the reaction mixture and azeotroped 3 times with acetonitrile before being dried for 12 hours under high vacuum. After dissolving in dry CH$_2$Cl$_2$, tetrazole (14.4 mL of a 0.45 M tetrazole solution in dry acetonitrile, 6.36 mmol) was added and the reaction mixture stirred for 1 hour at 22° C. and 2 hours at 35° C. An oxidizing solution of 0.2 M I$_2$ in THF/Pyr/H$_2$O was added with stirring until the solution remained yellow indicating that the reaction was fully oxidized, finally yielding compound 28. The reaction mixture was dried on high vacuum overnight before dissolving in CH$_2$Cl$_2$ and washing with 5% NaH$_2$CO$_3$ and water. Solvent was removed by rotoevaporation. The reaction mixture was dissolved in 0.14 M TEA (aq) and stirred for 3 hours. TEA was removed by high vacuum and water was removed by lyophilization overnight. 29 was extracted from the product mixture with MeOH. The solvent was removed and then 29 was extracted with $CH_2Cl_2$. A silica gel column (100% $CH_2Cl_2$-25/75 MeOH/ $CH_2Cl_2$) was utilized to yield 32 (2.72 g, 2.98 mmol) in a 70% yield. 29 was characterized by TLC (Rf=0.3 (1/9 MeOH/$CH_2Cl_2$), 31P-NMR (0.20 ppm), High Resolution FAB Mass Spectrometry ((M−H+) theoretical=913.5915/ observed=913.5945) 1H-NMR ($CDCl_3$) was also utilized for characterization. Peaks were observed at 7.35 (m), 5.77 (m), 5.65 (t), 5.28 (s), 5.20 (m), 5.08 (d), 5.00 (s), 4.63 (m), 4.460 (m), 4.307 (t), 4.23 (d), 2.17 (m), 4.09 (m), 3.02 (m), 3.73 (t), 3.57 (m), 3.37 (m), 2.79 (m), 2.72 (m), 2.30 (m), 1.57 (m), 1.24 (m), 0.86 (m) ppm.

β-D-ribofuranose 1-ethanolamine-2,3-myristoyl-5-phosphocholine, 30

29 (0.120 g, 0.131 mmol) was dissolved in 50/50 THF/MeOH in a quartz tube containing a stir bar. This reaction vessel was placed in a Rayonet Apparatus and irradiated at 254 nm for 4 hours with stirring. Solvent was removed by rotoevaporation and the product extracted into ether. The ether was rotoevaporated to a minimum and stored in the refrigerator overnight to provide a product containing precipitate. The mixture was purified utilizing a C18 SEP PAK™ column in 1/9 MeOH/ACN. The product has an Rf=0 in 65/25/4 $CH_2Cl_2$/MeOH/$H_2O$; therefore, it was difficult to determine its purity because of the presence of other impurities which also have an Rf of 0. A clean NMR was never obtained; however, very broad peaks in the sugar region as well as peaks in the tail region were observed. High Resolution FAB Mass Spectrometry ((M−H+) theoretical=779.5561/observed=779.5583) indicated product was formed.

References

The references listed below as well as all references cited in the specification are incorporated herein by reference to the extent that they supplement, explain, provide a background for or teach methodology, techniques and/or compositions employed herein.

Ahmad et al., *Chem. Phys. Lipids* 1990, 55, 231–243.

Bittman, *Chemical Synthesis of glycerophospholipds and their analogs*; Bittman, R., Ed.; CRC Press: Boca Raton, Fla., 1999, pp 185–207.

Blaurock et al., *Biochemistry* 1986, 25, 299–305.

Blume et al., *Biochim. Biophys. Acta.* 1981, 640, 609–618.

Browning, *NMR Studies of the Structural and Motional Properties of Phospholipids in Membranes*; Browning, J. L., Ed.; Elsevier/North-Holland Biomedical Press: New York, 1981; Vol. 47, pp 189–242.

Cao et al., *J. Biol. Chem.* 1987, 262, 16927–16935.

Dapergolas et al., *Lancet* 1976, Oct. 16, 824–827.

Deems et al., *Methods Enzym* 1981, 71, 703–710.

Deol et al., *Antimicrobial Agents & Chemotherapy* 1997, 41, 1211–4.

Eibl et al., *Biochim. Biophys. Acta.* 1979, 553, 476–488.

Engel, *Chem. Rev.* 1977, 77, 349–367.

Farhood et al., *Biochim. Biophys. Acta* 1995, 1235, 289–295.

Fuhrhop, *Chem. Rev.* 1993, 93, 1565–1582.

Gabizon et al., *Can. Res.* 1983, 43, 4730–4735.

Garnett, *Crit. Rev. Ther. Drug Carrier Sys.* 1999, 16, 147–207.

Gerasimov et al., *Triggered Release from Liposomes Mediated by Physically and Chemically Induced Phase Transitions*; Gerasimov, O. V.; Rui, Y.; Thompson, D. H., Ed.; Marcel Dekker, Inc.: New York, 1996; Vol. 62, pp 679–746.

Gregoriadis, *Liposomes*; Gregoriadis, G., Ed.; John Wright and Sons, Ltd.: Bristol, 1979, pp 287–349.

Haensler et al., *Bioconj. Chem.* 1993, 4, 372.

Han et al., *Molecular Therapy* 2000, 2, 302–317.

Hanahan, *A Guide to Phospholipid Chemistry*; Oxford University Press: New York, 1997.

Hanania et al., *Amer. J. Med.* 1995, 99, 537–552.

Hancock, *Methods. Enzym.* 1981, 72, 640–672.

Hird et al., *J Am. Chem. Soc.* 2000, 122, 8097–8098.

Honma et al., *Cancer. Chemother. Pharmacol.* 1983, 11, 73–76.

Huang et al., Introduction; Huang, L.; Viroonchatapan, E., Ed.; Academic Press: New York, 1999, pp 4–17.

Imae et al., *J. Am. Chem. Soc.* 1992, 114, 414–3419.

Israelachvili, *Intermolecular and Surface Forces*; Academic Press Inc.: San Diego, 1992.

Jacobson et al., *Biochemistry* 1975, 14, 152–161.

Juliano, *Pharmacokinetics of liposome-encapsulated drugs*; Juliano, R. L., Ed.; Elsevier/North-Holland Biomedical Press: New York, 1981, pp 391–407.

Kawana et al., *Bull. Chem. Soc. Jpn.* 1981, 54, 1492–1504.

Lasic, *Liposomes in Drug Delivery*; Lasic, D. D., Ed.; Marcel Dekker, Inc.: New York, 1996; Vol. 62, pp 447–476.

Lesney, *Modern Drug Discovery* 2000, 55–60.

Lister et al., *J. Lipid Research* 1988, 29, 1297–1308.

Litzenger et al., *Biochem. Biophys. Acta.* 1992, 1113, 201–227.

Marsh, *CRC Handbook of Lipid Bilayers*; CRC Press: Boca Raton, Fla., 1990.

McIntosh et al., *Biochim. Biophys. Acta* 1980, 597, 445–463.

McIntosh, *Biophys. J.* 1980, 29, 237–246.

McMullen et al., *Biochemistry* 1993, 32, 516–522.

Nayel et al., *Biochemistry* 1985, 24, 5967–5971.

Needham et al., *Biophys. J.* 1990, 58, 997–1009.

Needham et al., *Can. Res.* 2000, 60, 1197–1201.

Needham et al., *Chem. Rev.* 1995, 95, 2601.

Pack et al., *Biotech. and Bioeng.* 2000, 67, 217–223.

Porschke, *Biochemistry* 1984, 23, 4821.

Regen et al., *Biochem. and Biophys Research Comm.* 1981, 101, 131–136.

Rudolph, *Encapsulation of Hemoglobin in Liposomes*; Rudolph, A. S., Ed.; Birkhauser: Boston, 1995.

Silvius, *Cehm. Phys. Lipids* 1991, 57, 241–252.

Sommerdijk et al., *Chem. Eur. J.* 1998, 4, 127–136.

Srisiri et al., *J. Am. Chem. Soc.* 1996, 118, 11327–11328.

Suntres et al., *J. Drug Targeting* 1998, 6, 175–82.

Thomas et al., *J. Am. Chem. Soc.* 1998, 120, 12178–12186.

Trauble et al., *Proc. Nat Acad. Sci. USA* 1974, 71, 214–219.

U.S. Pat. No. 3,956,278.
U.S. Pat. No. 4,235,871.
U.S. Pat. No. 4,357,353.
U.S. Pat. No. 4,426,330.
U.S. Pat. No. 4,766,086.
U.S. Pat. No. 4,897,474.
U.S. Pat. No. 5,049,389.
U.S. Pat. No. 5,049,818.
U.S. Pat. No. 5,077,056.
U.S. Pat. No. 5,215,976.
U.S. Pat. No. 5,264,618.
U.S. Pat. No. 5,328,628.
U.S. Pat. No. 5,496,818.
U.S. Pat. No. 5,643,601.
U.S. Pat. No. 5,711,965.

Van Dijck et al., *Biochim. Biophys. Acta.* 1978, 512, 84–96.

Weinstein et al., *Self-Quenching of Carboxyfluorescein Fluorescence: Uses in Studying Liposome Stability and Liposome-Cell Interaction*; Weinstein, J. N.; Ralston, E.; Leserman, L. D.; Klausner, R. D.; Dragsten, P.; Henkart, P.; Blumenthal, R., Ed.; CRC Press, Inc.: Boca Raton, 1984; Vol. 3, pp 183–204.

Yant et al., *Nature Genetics* 2000, 25, 35–41.

Yuan et al., *J. Am. Chem. Soc.* 1987, 109, 8071–8081.

Zhao, *The Application of Electronic Pulse Delivery in Gene Therapy: Progress and Perspectives*; Zhao, X., Ed.; American Chemical Society: Washington D.C., 1996, pp 63–71.

It will be understood that various details of the invention may be changed without departing from the scope of the invention. Furthermore, the foregoing description is for the purpose of illustration only, and not for the purpose of limitation—the invention being defined by the claims.

What is claimed is:

1. A composition comprising a super molecular structure comprising a lipid compound having the formula:

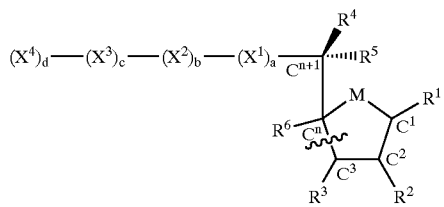

wherein:
each carbon of $C^{n+1}$ and $C^1$ to $C^n$ is a stereochemical center;
each carbon of $C^1$ to $C^n$ is a member of the heterocyclic ring containing M;
n=4, 5, 6, or 7;
$R^2$ and $R^3$ are the same or different, and are selected from the group consisting of amine, thiol, methoxy, straight or branched chain ester of 6–50 carbon atoms, straight or branched chain silane of 6–50 carbon atoms, straight or branched chain amide of 6–50 carbon atoms, straight or branched chain urea of 6–50 carbon atoms, straight or branched chain urethane of 6–50 carbon atoms, straight or branched chain carbonate of 6–50 carbon atoms, straight or branched chain sulfate of 6–50 carbon atoms, straight or branched chain thiol-urethane of 6–50 carbon atoms, straight or branched chain phosphate of 6–50 carbon atoms, straight or branched chain amine of 6–50 carbon atoms, straight or branched chain thio-urea of 6–50 carbon atoms, straight or branched chain thio-ether of 6–50 carbon atoms, straight or branched chain thio-ester of 6–50 carbon atoms, straight or branched chain ether of 6–50 carbon atoms, wherein any aforementioned chain is fully unsaturated, or comprises at least one carbon—carbon double bond;
$R^1$, $R^4$, $R^5$, and $R^6$ are the same or different, and are selected from the group consisting of H, OH, and the groups from which $R^2$ and $R^3$ may be selected;
M and $X^1$ are the same or different and are O, S, or N—$R^7$, wherein $R^7$ is H, a lower alkane, a chain as recited for $R^1$, $R^2$, or $R^3$, Se or any isoelectronic species of oxygen and a=0, 1, 2, 3, 4, 5, 6, 7, 8, 9, or 10;
$X^2$ is phosphonate, phosphate, boronophosphate, thiophosphate, or selenophosphate and b is 0, 1, 2, 3, 4, 5, 6, 7, 8, 9 or 10;
$X^3$=methylene or a monomer selected from the group consisting of an ether, an ester, an amine, a acrylic acid, amino acid, a nucleic acid, or a monosaccharide, and c=0, 1, 2, 3, 4, 5, 6, 7, 8, 9, 10, 11, 12, 13, 14, 15, 16, 17, 18, 19, or 20; and
$X^4$=hydroxide, N-succinyl derivative, a monomer selected from the group consisting of an amine, an ether, an ester, an amino acid, monosaccharide, and a nucleic acid, N—$(R^8)_e$ where $R^8$ is hydrogen or methylene chain of 1–20 carbons, or cyclic forms thereof and d=0, 1, 2, 3, 4, 5, 6, 7, 8, 9, 10 and e=1, 2 or 3;
wherein the supramolecular structure is selected from the group consisting of vesicles, liposomes, helixes, discs, tubes, fibers, toruses, hexagonal phases, micelles, gel phases, reverse micelles, microemulsions and emulsions.

2. The composition of claim 1, wherein the supramolecular structure is a liposome selected from the group consisting of multilamellar, single lamellar, and giant liposomes.

3. The composition of claim 1, wherein said supramolecular structure is formed from a combination of the lipid compound with from 0.1% to 99.9% of another material.

4. The composition of claim 3, wherein the other material is selected from the group consisting of DPPC, DMPC, PEGylated DPPC, fatty acids, cholesterol, fluorescently labeled phospholipids, ether lipids, sphingolipids, phospholipids, nucleic acids, polynucleic acids, amino acids, proteins, surfactants and combinations thereof.

5. The composition of claim 1, wherein said supramolecular structure further comprises an interior space that encapsulates a gas selected from the group consisting of air, $N_2$, $O_2$, $CO_2$, NO, and $C_fF_{2f+1}$, where f=1, 2, 3 or 4.

6. The composition of claim 1, wherein said supramolecular structure further comprises an interior space that encapsulates an aqueous solution selected from the group consisting of water, buffered aqueous media, saline, buffered saline, solutions of amino acids, solutions of sugars, solutions of vitamins, solutions of carbohydrates and combinations of any two or more thereof.

7. The composition of claim 1, wherein said supramolecular structure further comprises an interior space that encapsulates a non-aqueous liquid selected from the group consisting of soybean oil; mineral oil; corn oil; rapeseed oil; coconut oil; olive oil; safflower oil; cottonseed oil; aliphatic;

cycloaliphatic or aromatic hydrocarbons having 4–30 carbon atoms; aliphatic or aromatic alcohols having 2–30 carbon atoms; aliphatic or aromatic esters having 2–30 carbon atoms; alkyl; aryl or cyclic ethers having 2–30 carbon atoms; alkyl or aryl halides having 1–30 carbon atoms and having one or more halogen substituents; ketones having 3–30 carbon atoms; polyalkylene glycol; and combinations of any two or more thereof.

8. The composition of claim 1, wherein said supramolecular structure further comprises a solid particle.

9. The composition of claim 8, wherein the solid particle further comprises an active agent.

10. The composition of claim 8, wherein the solid particle further comprises a bioactive agent.

11. The composition of claim 8, wherein the solid particle further comprises a phospholipid, a nucleic acid, a polynucleic acid, an amino acid, a protein, a surfactant or any combination thereof.

12. The compound of claim 1, wherein the lipid compound is selected from the group consisting of bis-(2,3-lauroyl)-1-methoxy-5-(phosphocholine)-ribose (DLRPC), bis-(2, 3-myristoyl)-1-methoxy-5-(phosphocholine)-ribose (DMRPC), bis-(2,3-arachadonyl)-1-methoxy-5-(phosphocholine)-ribose (DARPC), bis-(2,3-lauroyl)-1-methoxy-5-ribo-phosphatidic acid (DLRPA), and 1-methoxy-2,3-dilauroyl-ribo-5-lysine (DLR-Lys).

13. A process for preparing a supramolecular structure composition suitable for use in carrying an active agent, the process comprising combining together an active agent and a supramolecular structure comprising a lipid compound having the formula:

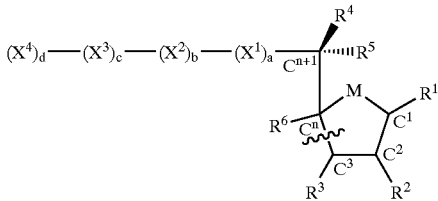

wherein:
each carbon of $C^{n+1}$ and $C^1$ to $C^n$ is a stereochemical center;
each carbon of $C^1$ to $C^n$ is a member of the heterocyclic ring containing M;
n=4, 5, 6 or 7;
$R^2$ and $R^3$ are the same or different, and are selected from the group consisting of amine, thiol, methoxy, straight or branched chain ester of 6–50 carbon atoms, straight or branched chain silane of 6–50 carbon atoms, straight or branched chain amide of 6–50 carbon atoms, straight or branched chain urea of 6–50 carbon atoms, straight or branched chain urethane of 6–50 carbon atoms, straight or branched chain carbonate of 6–50 carbon atoms, straight or branched chain sulfate of 6–50 carbon atoms, straight or branched chain thiol-urethane of 6–50 carbon atoms, straight or branched chain phosphate of 6–50 carbon atoms, straight or branched chain amine of 6–50 carbon atoms, straight or branched chain thio-urea of 6–50 carbon atoms, straight or branched chain thio-ether of 6–50 carbon atoms, straight or branched chain thio-ester of 6–50 carbon atoms, straight or branched chain ether of 6–50 carbon atoms, wherein any aforementioned chain is fully saturated, fully unsaturated, or comprises at least one carbon—carbon double bond;

$R^1$, $R^4$, $R^5$, and $R^6$ are the same or different, and are selected from the group consisting of H, OH, and the groups from which $R^2$ and $R^3$ may be selected;
M and $X^1$ are the same or different and are O, S, or N—$R^7$, wherein $R^7$ is H, a lower alkane, a chain as recited for $R^1$, $R^2$, or $R^3$, Se or any isoelectronic species of oxygen and a=0, 1, 2, 3, 4, 5, 6, 7, 8, 9, or 10;
$X^2$ is phosphonate, phosphate, boronophosphate, thiophosphate, or selenophosphate and b is 0, 1, 2, 3, 4, 5, 6, 7, 8, 9 or 10;
$X^3$=methylene or a monomer selected from the group consisting of an ether, an ester, an amine, acrylic acid, amino acid, a nucleic acid, or a monosaccharide, and c=0, 1, 2, 3, 4, 5, 6, 7, 8, 9, 10, 11, 12, 13, 14, 15, 16, 17, 18, 19, or 20; and
$X^4$=hydroxide, N-succinyl derivative, a monomer selected from the group consisting of an amine, an ether, an ester, an amino acid, monosaccharide, and a nucleic acid, N—$(R^8)_e$ where $R^8$ is hydrogen or methylene chain of 1–20 carbons, or cyclic forms thereof and d=0, 1, 2, 3, 4, 5, 6, 7, 8, 9, 10 and e=1, 2 or 3.

14. The process of claim 13, wherein the supramolecular structure composition is lyophilized.

15. The process of claim 13, wherein the supramolecular structure composition further comprises a micelle, a vesicle, a liposome, or mixtures thereof.

16. The process of claim 13, wherein the active agent is entrapped within an interior space of the supramolecular structure.

17. A process for the preparation of a supramolecular structure composition for the delivery of a bioactive agent, the process comprising combining together a bioactive agent and a supramolecular structure comprising a lipid compound having the formula:

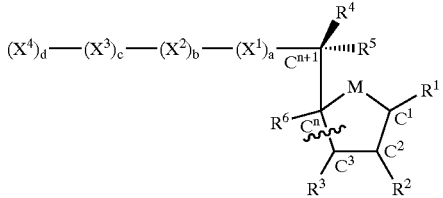

wherein:
each carbon of $C^{n+1}$ and $C^1$ to $C^n$ is a stereochemical center;
each carbon of $C^1$ to $C^n$ is a member of the heterocyclic ring containing M;
n=4, 5, 6 or 7;
$R^2$ and $R^3$ are the same or different, and are selected from the group consisting of amine, thiol, methoxy, straight or branched chain ester of 6–50 carbon atoms, straight or branched chain silane of 6–50 carbon atoms, straight or branched chain amide of 6–50 carbon atoms, straight or branched chain urea of 6–50 carbon atoms, straight or branched chain urethane of 6–50 carbon atoms, straight or branched chain carbonate of 6–50 carbon atoms, straight or branched chain sulfate of 6–50 carbon atoms, straight or branched chain thiol-urethane of 6–50 carbon atoms, straight or branched chain phosphate of 6–50 carbon atoms, straight or branched chain amine of 6–50 carbon atoms, straight or branched chain thio-urea of 6–50 carbon atoms, straight or branched chain thio-ether of 6–50 carbon atoms, straight or branched chain thio-ester of 6–50 carbon atoms, straight or branched chain ether of 6–50 atoms, wherein any aforementioned chain is fully saturated, fully unsaturated, or comprises at least one carbon—carbon double bond;

$R^1$, $R^4$, $R^5$, and $R^6$ are the same or different, and are selected from the group consisting of H, OH, and the groups from which $R^2$ and $R^3$ may be selected;

M and $X^1$ are the same or different and are O, S, or N—$R^7$, wherein $R^7$ is H, a lower alkane, a chain as recited for $R^1$, $R^2$, or $R^3$, Se or any isoelectronic species of oxygen and a=0, 1, 2, 3, 4, 5, 6, 7, 8, 9, or 10;

$X^2$ is phosphonate, phosphate, boronophosphate, thiophosphate, or selenophosphate and b is 0, 1, 2, 3, 4, 5, 6, 7, 8, 9 or 10;

$X^3$=methylene or a monomer selected from the group consisting of an ether, an ester, an amine, acrylic acid, amino acid, a nucleic acid, or a monosaccharide, and c=0, 1, 2, 3, 4, 5, 6, 7, 8, 9, 10, 11, 12, 13, 14, 15, 16, 17, 18, 19, or 20; and $X^4$=hydroxide, N-succinyl derivative, a monomer selected from the group consisting of an amine, an ether, an ester, an amino acid, monosaccharide, and a nucleic acid, N—$(R^8)_e$ where $R^8$ is hydrogen or methylene chain of 1–20 carbons, or cyclic forms thereof and d=0, 1, 2, 3, 4, 5, 6, 7, 8, 9, 10 and e=1, 2 or 3.

18. The process of claim 17, wherein the supramolecular structure composition is lyophilized.

19. The process of claim 17, wherein the supramolecular structure composition further comprises a micelle, a vesicle, a liposome, or mixtures thereof.

20. The process of claim 17, wherein the active agent is entrapped within an interior space of the supramolecular structure.

21. A lipid compound comprising:

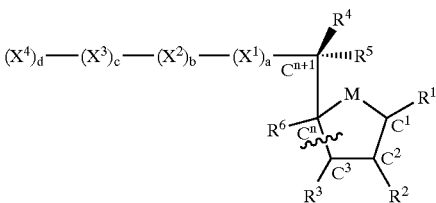

wherein:
each carbon of $C^{n+1}$ and $C^1$ to $C^n$ is a stereochemical center;
each carbon of $C^1$ to $C^n$ is a member of the heterocyclic ring containing M;
n=6 or 7;
$R^1$, $R^2$, $R^3$, $R^4$, $R^5$, and $R^6$ are the same or different, and are selected from the group consisting of H, OH, amine, thiol, methoxy, straight or branched chain ester of 6–50 carbon atoms, straight or branched chain silane of 6–50 carbon atoms, straight or branched chain amide of 6–50 carbon atoms, straight or branched chain urea of 6–50 carbon atoms, straight or branched chain urethane of 6–50 carbon atoms, straight or branched chain carbonate of 6–50 carbon atoms, straight or branched chain sulfate of 6–50 carbon atoms, straight or branched chain thiol-urethane of 6–50 carbon atoms, straight or branched chain phosphate of 6–50 carbon atoms, straight or branched chain amine of 6–50 carbon atoms, straight or branched chain thio-urea of 6–50 carbon atoms, straight or branched chain thio-ether of 6–50 carbon atoms, straight or branched chain thio-ester of 6–50 carbon atoms, straight or branched chain ether of 6–50 carbon atoms, wherein any aforementioned chain is fully saturated, fully unsaturated, or comprises at least one carbon—carbon double bond;

M and $X^1$ are the same or different and are O, S, or N—$R^7$, wherein $R^7$ is H, a lower alkane, a chain as recited for $R^1$, $R^2$, or $R^3$, Se or any isoelectronic species of oxygen and a=0, 1, 2, 3, 4, 5, 6, 7, 8, 9, or 10;

$X^2$ is phosphonate, phosphate, boronophosphate, thiophosphate, or selenophosphate and b is 0, 1, 2, 3, 4, 5, 6, 7, 8, 9 or 10;

$X^3$=methylene or a monomer selected from the group consisting of an ether, an ester, an amine, acrylic acid, amino acid, a nucleic acid, or a monosaccharide, and c=0, 1, 2, 3, 4, 5, 6, 7, 8, 9, 10, 11, 12, 13, 14, 15, 16, 17, 18, 19, or 20; and $X^4$=hydroxide, N-succinyl derivative, a monomer selected from the group consisting of an amine, an ether, an ester, an amino acid, monosaccharide, and a nucleic acid, N—$(R^8)_e$ where $R^8$ is hydrogen or methylene chain of 1–20 carbons, or cyclic forms thereof and d=0, 1, 2, 3, 4, 5, 6, 7, 8, 9, 10 and e=1, 2 or 3.

22. The compound of claim 21, wherein $R^1$–$R^7$ are the same or different and are alkanes, alkenes, alkynes or halo-substituted version thereof, wherein halo is F, I, Cl, or Br.

23. The compound of claim 21, wherein $R^1$–$R^7$ are the same or different and terminate in an amine, thiol, amide, phosphate, sulphate, hydroxide or —SeH.

24. The compound of claim 21, wherein $R^1$–$R^7$ are the same or different and comprise a chain length of 10–24 carbon atoms.

25. The compound of claim 21, wherein an antibody is attached to one of $R^1$, $R^2$, $R^3$, $X^1$, $X^2$, $X^3$, $X^4$, $R^4$, $R^5$ and $R^6$, or a combination thereof.

26. The compound of claim 21, wherein a nucleotide is attached to one of $R^1$, $R^2$, $R^3$, $X^1$, $X^2$, $X^3$, $X^4$, $R^4$, $R^5$ and $R^6$, or a combination thereof.

27. The compound of claim 21, wherein a nucleoside is attached to one of $R^1$, $R^2$, $R^3$, $X^1$, $X^2$, $X^3$, $X^4$, $R^4$, $R^5$ and $R^6$, or a combination thereof.

28. The compound of claim 21, wherein an oligonucleotide is attached to one of $R^1$, $R^2$, $R^3$, $X^1$, $X^2$, $X^3$, $X^4$, $R^4$, $R^5$ and $R^6$, or a combination thereof.

29. The compound of claim 21, wherein a contrast agent is attached to one of $R^1$, $R^2$, $R^3$, $X^1$, $X^2$, $X^3$, $X^4$, $R^4$, $R^5$ and $R^6$, or a combination thereof.

30. The compound of claim 29, wherein the contrast agent is a tomography agent or a magnetic resonance imaging agent.

31. The compound of claim 29, wherein the contrast agent is an iodated compound attached for X-ray imaging.

32. The compound of claim 21, wherein a ligand is attached to one of $R^1$, $R^2$, $R^3$, $X^1$, $X^2$, $X^3$, $X^4$, $R^4$, $R^5$ and $R^6$, or a combination thereof.

33. The compound of claim 21, wherein a bioactive agent is attached to one of $R^1$, $R^2$, $R^3$, $X^1$, $X^2$, $X^3$, $X^4$, $R^4$, $R^5$ and $R^6$, or a combination thereof.

34. The compound of claim 33, wherein the bioactive agent is an antibacterial, anticancer, anti-inflammatory, or antiviral.

35. The compound of claim 21, wherein a carbohydrate is attached to one of $R^1, R^2, R^3, X^1, X^2, X^3, X^4, R^4, R^5$ and $R^6$, or a combination thereof.

36. The compound of claim 35, wherein the carbohydrate is mannose or sialic acid.

37. The compound of claim 21, wherein $(X^1)_a$—$(X^2)_b$—$(X^3)_c$—$(X^4)_d$ replaces or substitutes 1 or more of $R^1$, $R^2$, or $R^3$.

38. A lipid compound comprising:

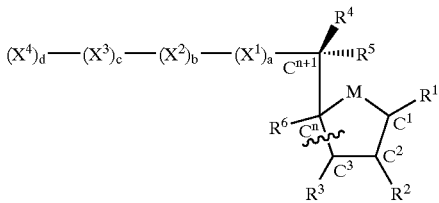

wherein:
each carbon of $C^{n+1}$ and $C^1$ to $C^n$ is a stereochemical center;
each carbon of $C^1$ to $C^n$ is a member of the heterocyclic ring containing M;
n=5;
$R^2$ and $R^3$ are the same or different, and are selected from the group consisting of amine, thiol, methoxy, straight or branched chain ester of 6–50 carbon atoms, straight or branched chain silane of 6–50 carbon atoms, straight or branched chain amide of 6–50 carbon atoms, straight or branched chain urea of 6–50 carbon atoms, straight or branched chain urethane of 6–50 carbon atoms, straight or branched chain carbonate of 6–50 carbon atoms, straight or branched chain sulfate of 6–50 carbon atoms, straight or branched chain thiol-urethane of 6–50 carbon atoms, straight or branched chain phosphate of 6–50 carbon atoms, straight or branched chain amine of 6–50 carbon atoms, straight or branched chain thio-urea of 6–50 carbon atoms, straight or branched chain thio-ether of 6–50 carbon atoms, straight or branched chain thio-ester 6–50 carbon atoms, straight or branched chain ether of 6–50 carbon atoms, wherein any aforementioned chain is fully saturated, fully unsaturated, or comprises at least one carbon—carbon double bond;
$R^1$, $R^4$, $R^5$, and $R^6$ are the same or different, and are selected from the group consisting of H, OH, and the groups from which $R^2$ and $R^3$ may be selected;
M and $X^1$ are the same or different and are O, S, or N—$R^7$, wherein $R^7$ is H, a lower alkane, a chain as recited for $R^1$, $R^2$, or $R^3$, Se or any isoelectronic species of oxygen and a=0, 1, 2, 3, 4, 5, 6, 7, 8, 9, or 10;
$X^2$ is phosphonate, phosphate, boronophosphate, thiophosphate, or selenophosphate and b is 0, 1, 2, 3, 4, 5, 6, 7, 8, 9 or 10;
$X^3$=methylene or a monomer selected from the group consisting of an ether, an ester, an amine, acrylic acid, amino acid, a nucleic acid, or a monosaccharide, and c=0, 1, 2, 3, 4, 5, 6, 7, 8, 9, 10, 11, 12, 13, 14, 15, 16, 17, 18, 19, or 20; and
$X^4$=hydroxide, N-succinyl derivative, a monomer selected from the group consisting of an amine, an ether, an ester, an amino acid, monosaccharide, and a nucleic acid, N—$(R^8)_e$ where $R^8$ is hydrogen or methylene chain of 1–20 carbons, or cyclic forms thereof and d=0, 1, 2, 3, 4, 5, 6, 7, 8, 9, 10 and e=1, 2 or 3.

39. The compound of claim 38, wherein $R^1$–$R^7$ are the same or different and are alkanes, alkenes, alkynes or halo-substituted version thereof wherein halo is F, I, Cl, or Br.

40. The compound of claim 38, wherein $R^1$–$R^7$ are the same or different and terminate in an amine, thiol, amide, phosphate, sulphate, hydroxide or —SeH.

41. The compound of claim 38, wherein $R^1$–$R^7$ are the same or different and comprise a chain length of 10–24 carbon atoms.

42. The compound of claim 38, wherein an antibody is attached to one of $R^1, R^2, R^3, X^1, X^2, X^3, X^4, R^4, R^5$ and $R^6$, or a combination thereof.

43. The compound of claim 38, wherein a nucleotide is attached to one of $R^1, R^2, R^3, X^1, X^2, X^3, X^4 R^4, R^5$ and $R^6$, or a combination thereof.

44. The compound of claim 38, wherein a nucleoside is attached to one of $R^1, R^2, R^3, X^1, X^2, X^3, X^4, R^4, R^5$ and $R^6$, or a combination thereof.

45. The compound of claim 38, wherein an oligonucleotide is attached to one of $R^1, R^2, R^3, X^1, X^2, X^3, X^4, R^4, R^5$ and $R^6$, or a combination thereof.

46. The compound of claim 38, wherein a contrast agent is attached to one of $R^1, R^2, R^3, X^1, X^2, X^3, X^4, R^4, R^5$ and $R^6$, or a combination thereof.

47. The compound of claim 46, wherein the contrast agent is a tomography agent or a magnetic resonance imaging agent.

48. The compound of claim 46, wherein the contrast agent is an iodated compound attached for X-ray imaging.

49. The compound of claim 38, wherein a ligand is attached to one of $R^1, R^2, R^3, X^1, X^2, X^3, X^4, R^4, R^5$ and $R^6$, or a combination thereof.

50. The compound of claim 38, wherein a bioactive agent is attached to one of $R^1, R^2, R^3, X^1, X^2, X^3, X^4, R^4, R^5$ and $R^6$, or a combination thereof.

51. The compound of claim 50, wherein the bioactive agent is an antibacterial, anticancer, anti-inflammatory, or antiviral.

52. The compound of claim 38, wherein a carbohydrate is attached to one of $R^1, R^2, R^3, X^1, X^2, X^3, X^4, R^4, R^5$ and $R^6$, or a combination thereof.

53. The compound of claim 52, wherein the carbohydrate is mannose or sialic acid.

54. The compound of claim 38, wherein $(X^1)_a$—$(X^2)_b$—$(X^3)_c$—$(X^4)_d$ replaces or substitutes 1 or more of $R^1$, $R^2$, or $R^3$.

55. A lipid compound comprising:

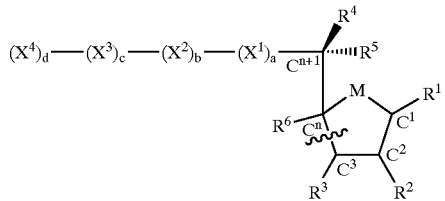

wherein:
each carbon of $C^{n+1}$ and $C^1$ to $C^n$ is a stereochemical center;
each carbon of $C^1$ to $C^n$ is a member of the heterocyclic ring containing M;
n=4;
$R^1, R^2, R^3, R^4, R^5$, and $R^6$ are the same or different, and are selected from the group consisting of H, OH, amine, thiol, methoxy, straight or branched chain ester of 6–50 carbon atoms, straight or branched chain silane of 6–50 carbon atoms, straight or branched chain amide of 6–50 carbon atoms, straight or branched chain urea of 6–50 carbon atoms, straight or branched chain urethane of 6–50 carbon atoms, straight or branched chain carbonate of 6–50 carbon atoms, straight or branched chain sulfate of 6–50 carbon atoms, straight or branched chain thiol-urethane of 6–50 carbon atoms, straight or branched chain phosphate of 6–50 carbon atoms, straight or branched chain amine of 6–50 carbon atoms, straight or branched chain thio-urea of 6–50 carbon atoms, straight or branched chain thio-ether of 6–50 carbon atoms, straight or branched chain thio-ester 6–50 carbon atoms, straight or branched chain ether of 6–50 carbon atoms, wherein any aforementioned chain is fully saturated, fully unsaturated, or comprises at least one carbon—carbon double bond;

M and $X^1$ are the same or different and are O, S, or N—$R^7$, wherein $R^7$ is H, a lower alkane, a chain as recited for $R^1$, $R^2$, or $R^3$, Se or any isoelectronic species of oxygen and a=0, 1, 2, 3, 4, 5, 6, 7, 8, 9, or 10;

$X^2$ is phosphonate, phosphate, boronophosphate, thio-phosphate, or selenophosphate and b is 0, 1, 2, 3, 4, 5, 6, 7, 8, 9 or 10;

$X^3$=a monomer selected from the group consisting of an ether, an ester, an amine, acrylic acid, amino acid, a nucleic acid, or a monosaccharide, and c=1, 2, 3, 4, 5, 6, 7, 8, 9, 10, 11, 12, 13, 14, 15, 16, 17, 18, 19, or 20; and $X^4$=hydroxide, N-succinyl derivative, a monomer selected from the group consisting of an ether, an ester, an amino acid, monosaccharide, and a nucleic acid, and d=1, 2, 3, 4, 5, 6, 7, 8, 9, 10.

56. The compound of claim 55, wherein the chains of $R^1$–$R^7$ are the same or different and are alkanes, alkenes, alkynes or halo-substituted version thereof, wherein halo is F, I, Cl, or Br.

57. The compound of claim 55, wherein the chains of $R^1$–$R^7$ are the same or different and terminate in an amine, thiol, amide, phosphate, sulphate, hydroxide or —SeH.

58. The compound of claim 55, wherein the chains of $R^1$–$R^7$ are the same or different and comprise a chain length of 10–24 carbon atoms.

59. The compound of claim 55, wherein an antibody is attached to one of $R^1$, $R^2$, $R^3$, $X^1$, $X^2$, $X^3$, $X^4$, $R^4$, $R^5$ and $R^6$, or a combination thereof.

60. The compound of claim 55, wherein a nucleotide is attached to one of $R^1$, $R^2$, $R^3$, $X^1$, $X^2$, $X^3$, $X^4$, $R^4$, $R^5$ and $R^6$, or a combination thereof.

61. The compound of claim 55, wherein a nucleoside is attached to one of $R^1$, $R^2$, $R^3$, $X^1$, $X^2$, $X^3$, $X^4$, $R^4$, $R^5$ and $R^6$, or a combination thereof.

62. The compound of claim 55, wherein an oligonucleotide is attached to one of $R^1$, $R^2$, $R^3$, $X^1$, $X^2$, $X^3$, $X^4$, $R^4$, $R^5$ and $R^6$, or a combination thereof.

63. The compound of claim 55, wherein a contrast agent is attached to one of $R^1$, $R^2$, $R^3$, $X^1$, $X^2$, $X^3$, $X^4$, $R^4$, $R^5$ and $R^6$, or a combination thereof.

64. The compound of claim 63, wherein the contrast agent is a tomography agent or a magnetic resonance imaging agent.

65. The compound of claim 63, wherein the contrast agent is an iodated compound attached for X-ray imaging.

66. The compound of claim 55, wherein a ligand is attached to one of $R^1$, $R^2$, $R^3$, $X^1$, $X^2$, $X^3$, $X^4$, $R^4$, $R^5$ and $R^6$, or a combination thereof.

67. The compound of claim 55, wherein a bioactive agent is attached to one of $R^1$, $R^2$, $R^3$, $X^1$, $X^2$, $X^3$, $X^4$, $R^4$, $R^5$ and $R^6$, or a combination thereof.

68. The compound of claim 67, wherein the bioactive agent is an antibacterial, anticancer, anti-inflammatory, or antiviral.

69. The compound of claim 55, wherein a carbohydrate is attached to one of $R^1$, $R^2$, $R^3$, $X^1$, $X^2$, $X^3$, $X^4$, $R^4$, $R^5$ and $R^6$, or a combination thereof.

70. The compound of claim 69, wherein the carbohydrate is mannose or sialic acid.

71. The compound of claim 55, wherein $(X^1)_a$—$(X^2)_b$—$(X^3)_c$—$(X^4)_d$ replaces or substitutes 1 or more of $R^1$, $R^2$, or $R^3$.

72. The compound of claim 55, wherein the compound is selected from the group consisting of bis-(2,3lauroyl)-1-methoxy-5-ribo-phosphatidic acid (DLRPA) and 1-methoxy-2,3-dilauroyl-ribo-5-lysine (DLR-Lys).

* * * * *